US009382382B2

(12) United States Patent
   Kuhlman

(10) Patent No.: US 9,382,382 B2
(45) Date of Patent: Jul. 5, 2016

(54) POLYETHERIMIDES, METHODS OF MANUFACTURE, AND ARTICLES FORMED THEREFROM

(71) Applicant: SABIC Innovative Plastics IP B.V., Bergen op Zoom (NL)

(72) Inventor: Matthew L. Kuhlman, Evansville, IN (US)

(73) Assignee: SABIC GLOBAL TECHNOLOGIES B.V. (NL)

( * ) Notice: Subject to any disclaimer, the term of this patent is extended or adjusted under 35 U.S.C. 154(b) by 294 days.

(21) Appl. No.: 14/026,312

(22) Filed: Sep. 13, 2013

(65) Prior Publication Data
   US 2015/0079376 A1    Mar. 19, 2015

(51) Int. Cl.
   *C08G 73/00* (2006.01)
   *C08G 73/10* (2006.01)
   *C07D 209/48* (2006.01)
   *C08L 79/08* (2006.01)
   *C09D 179/08* (2006.01)
   *C08K 5/51* (2006.01)
   *D01F 6/74* (2006.01)

(52) U.S. Cl.
   CPC .......... *C08G 73/1071* (2013.01); *C07D 209/48* (2013.01); *C08G 73/1003* (2013.01); *C08G 73/1046* (2013.01); *C08G 73/1053* (2013.01); *C08G 73/1067* (2013.01); *C08K 5/51* (2013.01); *C08L 79/08* (2013.01); *C09D 179/08* (2013.01); *C08J 2379/08* (2013.01); *D01F 6/74* (2013.01)

(58) Field of Classification Search
   CPC .. C08L 79/08; C08G 73/1046; C07D 209/48; C08J 2379/08; C09D 179/08
   See application file for complete search history.

(56) References Cited

U.S. PATENT DOCUMENTS

| | | | |
|---|---|---|---|
| 3,383,092 A | 5/1968 | Cazier | |
| 3,609,123 A | 9/1971 | Rabilloud et al. | |
| 3,671,487 A | 6/1972 | Abolins | |
| 3,723,373 A | 3/1973 | Lucas | |
| 3,787,364 A | 1/1974 | Wirth et al. | |
| 3,838,097 A | 9/1974 | Wirth et al. | |
| 3,847,867 A | 11/1974 | Heath et al. | |
| 4,217,438 A | 8/1980 | Brunelle et al. | |
| 4,417,044 A | 11/1983 | Parekh | |
| 4,460,778 A | 7/1984 | Brunelle | |
| 4,546,207 A | 10/1985 | Mendiratta et al. | |
| 4,611,048 A | 9/1986 | Peters | |
| 4,757,150 A | 7/1988 | Guggenheim et al. | |
| 4,851,495 A | 7/1989 | Sheppard et al. | |
| 4,870,155 A | 9/1989 | Matzner et al. | |
| 4,950,729 A | 8/1990 | Daniels | |
| 4,988,544 A | 1/1991 | Cella et al. | |
| 4,999,251 A | 3/1991 | Foust et al. | |
| 5,028,681 A | 7/1991 | Peters | |
| 5,061,780 A | 10/1991 | Wang | |
| 5,064,921 A | 11/1991 | Blum et al. | |
| 5,101,006 A | 3/1992 | Stults et al. | |

(Continued)

FOREIGN PATENT DOCUMENTS

| | | |
|---|---|---|
| CN | 1867613 | 11/2006 |
| CN | 1919894 A | 2/2007 |

(Continued)

OTHER PUBLICATIONS

English Abstract of CN 1367192 A; Date of Publication Sep. 4, 2002; 1 page.

(Continued)

*Primary Examiner* — Gregory Listvoyb
(74) *Attorney, Agent, or Firm* — Cantor Colburn LLP

(57) ABSTRACT

A polyetherimide composition comprising a polyetherimide manufactured by reaction of an alkali metal salt of a dihydroxy aromatic compound with a bis(halophthalimide) composition comprising, based on the weight of the bis(halophthalimide) composition, at least 15 wt. % of a 3,3'-bis (halophthalimide) of the formula

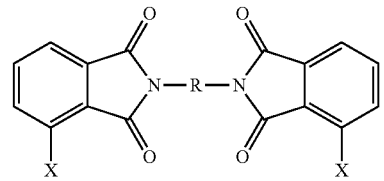

from more than 17 wt. % to less than 85 wt. % of a 4,3'-bis (halophthalimide) of the formula

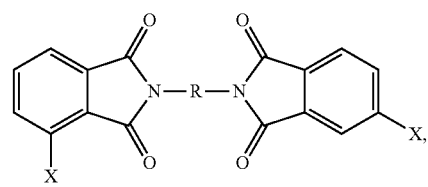

and
from more than 0 to less than 27 wt. % of a 4,4'-bis(halophthalimide) of the formula

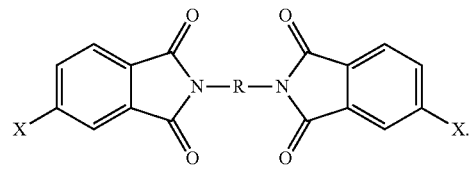

19 Claims, 1 Drawing Sheet

(56) References Cited

U.S. PATENT DOCUMENTS

| | | |
|---|---|---|
| 5,229,482 A | 7/1993 | Brunelle |
| 5,246,751 A | 9/1993 | White et al. |
| 5,304,627 A | 4/1994 | Connell et al. |
| 5,521,230 A | 5/1996 | Bhatia et al. |
| 5,663,275 A | 9/1997 | Schmidhauser |
| 5,830,974 A | 11/1998 | Schmidhauser et al. |
| 5,856,421 A | 1/1999 | Schmidhauser |
| 5,908,915 A | 6/1999 | Brunelle |
| 5,917,005 A | 6/1999 | Brunelle et al. |
| 6,020,456 A | 2/2000 | Brunelle et al. |
| 6,235,866 B1 | 5/2001 | Khouri et al. |
| 6,498,224 B1 | 12/2002 | Odle et al. |
| 6,657,068 B2 | 12/2003 | Colborn et al. |
| 6,849,706 B1 | 2/2005 | Brunelle et al. |
| 6,881,815 B2 | 4/2005 | Odle et al. |
| 6,906,168 B2 | 6/2005 | Khouri et al. |
| 6,919,418 B2 | 7/2005 | Khouri et al. |
| 7,125,954 B2 | 10/2006 | Guggenheim et al. |
| 7,481,959 B2 | 1/2009 | Richards et al. |
| 7,605,222 B2 | 10/2009 | Ye et al. |
| 7,714,095 B2 | 5/2010 | Brunelle et al. |
| 8,309,637 B2 | 11/2012 | Sanner et al. |
| 8,357,773 B1 | 1/2013 | Gallucci et al. |
| 8,524,854 B2 | 9/2013 | Chiong et al. |
| 8,907,042 B2 | 12/2014 | Kuhlman et al. |
| 9,045,636 B2 | 6/2015 | Gallucci et al. |
| 9,127,128 B2 | 9/2015 | Kuhlman et al. |
| 2002/0091204 A1 | 7/2002 | Fehnel et al. |
| 2004/0019174 A1 | 1/2004 | Ichiroku et al. |
| 2005/0043493 A1 | 2/2005 | Smith et al. |
| 2006/0004223 A1 | 1/2006 | Colborn et al. |
| 2006/0135731 A1 | 6/2006 | Silva et al. |
| 2006/0135733 A1 | 6/2006 | Khouri et al. |
| 2011/0065891 A1 | 3/2011 | Fang et al. |
| 2011/0263791 A1 | 10/2011 | Chiong et al. |
| 2012/0029125 A1 | 2/2012 | Gallucci et al. |
| 2012/0287555 A1 | 11/2012 | Silvi et al. |
| 2013/0053489 A1 | 2/2013 | Gallucci et al. |
| 2013/0108851 A1 | 5/2013 | Kuhlman et al. |
| 2013/0108852 A1 | 5/2013 | Kuhlman et al. |
| 2013/0303698 A1 | 11/2013 | Chiong et al. |
| 2015/0073116 A1 | 3/2015 | Kuhlman et al. |
| 2015/0079376 A1 | 3/2015 | Kuhlman |

FOREIGN PATENT DOCUMENTS

| | | |
|---|---|---|
| EP | 0132547 B1 | 2/1989 |
| EP | 0892003 A2 | 1/1999 |
| EP | 1403303 B1 | 8/2008 |
| EP | 1660559 B1 | 9/2009 |
| EP | 1426358 B1 | 1/2010 |
| EP | 2644641 A | 10/2013 |
| GB | 1392649 | 4/1975 |
| GB | 1485172 | 9/1977 |
| WO | 2009143440 A1 | 11/2009 |
| WO | 2011082147 A1 | 7/2011 |

OTHER PUBLICATIONS

English Abstract of CN 1560113 A; Date of Publication Jan. 5, 2005; 1 page.

English Abstract of CN 1803888 A; Date of Publication Jul. 19, 2006; 1 page.

International Search Report, International Application No. PCT/US2014/055324; International Filing Date, Sep. 12, 2014; Date of Mailing, Nov. 27, 2014; (P070342PCT); 4 pages.

Written Opinion of International Searching Authority, International Application No. PCT/US2014/055324; International Filing Date, Sep. 12, 2014; Date of Mailing, Nov. 27, 2014; (P070342PCT); 5 pages.

International Search Report for International Application No. PCT/US2010/062191, Application Filing Date Dec. 28, 2010; Date of Mailing Mar. 23, 2011, 4 pages.

Non Final Office Action, Issued Apr. 17, 2015, P070122USC.

Office Action Issued Feb. 24, 2015 in P070122JP.

Quafisheh et al., Potassium Phosphate as a High-Performance Solid Base in Phase-Transfer-Catalyzed Alkylation Reactions, Ind. Eng. Chem. Res. 2007, 46, 3016-3023.

Written Opinion for International Application No. PCT/US2010/062191, Application Filing Date: Dec. 28, 2010; Date of Mailing: Mar. 23, 2011, 6 pages.

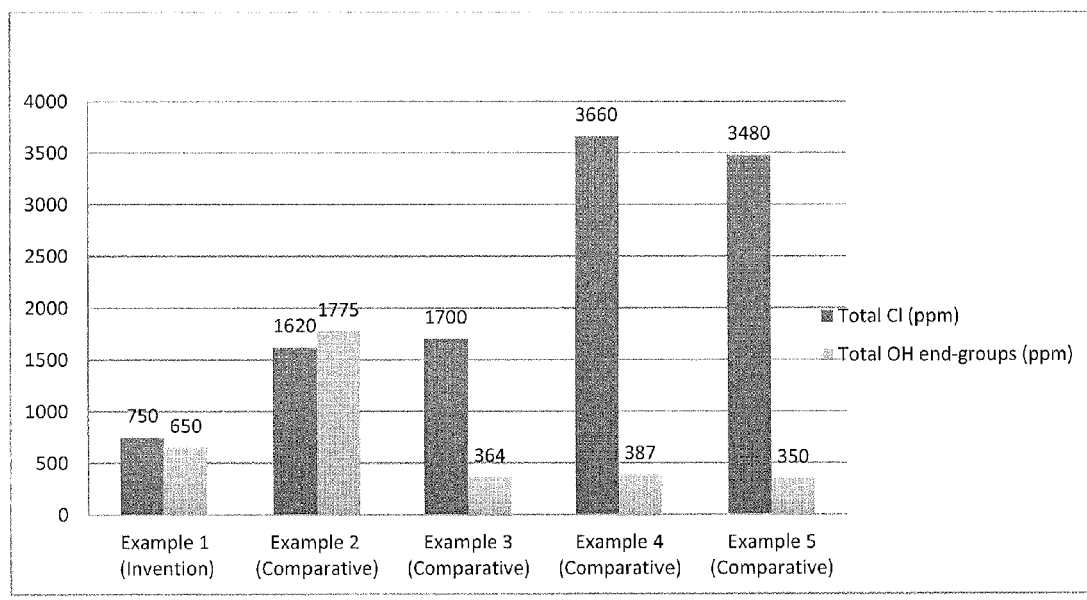
summarizes the substantially less chlorine and OH substituents that compositions of our invention exhibited as compared to compositions used in Comparative Examples 2-5.

POLYETHERIMIDES, METHODS OF MANUFACTURE, AND ARTICLES FORMED THEREFROM

BACKGROUND OF THE INVENTION

This disclosure relates to polyetherimides and compositions containing the polyetherimides, as well as their method of manufacture and articles formed from the polyetherimide compositions.

Polyetherimides ("PEIs") are amorphous, transparent, high performance polymers having a glass transition temperature ("Tg") of greater than 180° C. PEIs further have high strength, heat resistance, and modulus, and broad chemical resistance, and so are widely used in applications as diverse as automotive, telecommunication, aerospace, electrical/electronics, transportation, and healthcare.

Polyetherimides can be manufactured commercially by a "halo-displacement process." A halogen-substituted anhydride is reacted with a diamine to form a bishalophthalimide. The bishalophthalimide is then reacted with a metal salt of a dihydroxy compound. Despite extensive investigation into the manufacture of polyetherimides produced using the halo-displacement process, there nonetheless remains a need for further improvement. For example, chloro-displacement technology allows the ratio of the 4 and 3 ether linkages of the polymer to be significantly altered. The earlier nitration process is limited to high 4-isomer content, only a 95:5 isomer ratio of the 4:3 isomers can be obtained. The halo-displacement process allows for a polyetherimide material with any ratio of 4 and 3 ether linkages in the polymer; however, the halide level is above the 900 ppm level required for use in electrical/electronics applications.

There accordingly remains a need in the art for methods for the manufacture of polyetherimides having improved properties, in particular polyetherimides having improved Tg and flow, but with reduced levels of byproducts, including halogenated byproducts and cyclic byproducts. It would be a further advantage if such improvements were obtained without significantly adversely affecting other desirable properties of the polyetherimides, for example, one or more of heat deflection temperature, Vicat, and high tensile strength at yield.

SUMMARY OF THE INVENTION

In an embodiment, a polymer composition comprising a polyetherimide having the formula

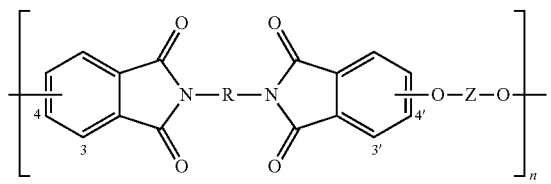

wherein n is greater than 1, each R is the same or different, and is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

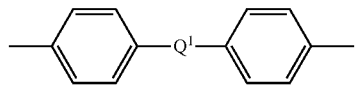

wherein $Q^1$ is selected from —O—, —S—, —C(O)—, —SO$_2$—, —SO—, and —C$_y$H$_{2y}$— wherein y is 1 to 5 and a halogenated derivative thereof, each Z is the same or different, and is an aromatic C$_{6-24}$ monocyclic or polycyclic moiety optionally substituted with 1 to 6 C$_{1-18}$ alkyl groups, 1 to 8 halogen atoms, or a combination thereof, and the divalent bonds between the —O—Z—O— group and the phenyl substituents are in the 3,3', 3,4', 4,3', and 4,4' positions, the divalent bonds of the —O—Z—O— group being made from a bis(halophthalimide) composition comprising, based on the weight of the bis(halophthalimide) composition, at least 15 wt. % of a 3,3'-bis(halophthalimide) of the formula

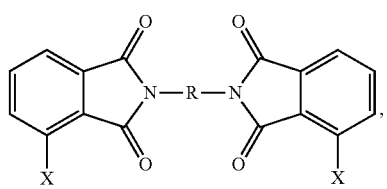

from more than 17 wt. % to less than 85 wt. % of a 4,3'-bis(halophthalimide) of the formula

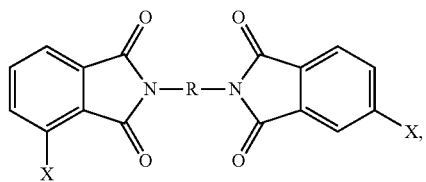

and
from more than 0 to less than 27 wt. % of a 4,4'-bis(halophthalimide) of the formula

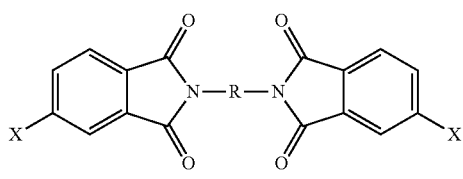

wherein each X is independently fluoro, chloro, bromo, or iodo and R is as defined above, the polyetherimide being a catalyzed polymerization reaction product of the bis(halophthalimide) composition and a 1.6 to 2.0 mole % excess of an alkali metal salt of a dihydroxy aromatic compound of the formula

MO—Z—OM wherein M is an alkali metal, and Z is as defined above, in the presence of from 2 to 4 mole % of an endcapping agent, and wherein the polyetherimide has: a Tg above 220° C.; 20 to 35 wt. % solids; an Mw of at least 42,000 Daltons; a maximum chloride content of 900, preferably 750 ppm by weight; a maximum of 700, preferably 650 ppm by weight OH end-group polymer functionality; and the low shear viscosity of the polyetherimide is at least 30% lower than a polyetherimide made from a bis(halophthalimide) composition comprising less than 10 wt. % of the 4,3'-bis(halophthalimide).

In another embodiment, the polymer composition comprises from more than 47 wt. % to less than 85 wt. % of the 4,3'-bis(halophthalimide).

In another embodiment, R is a divalent radical of the formula

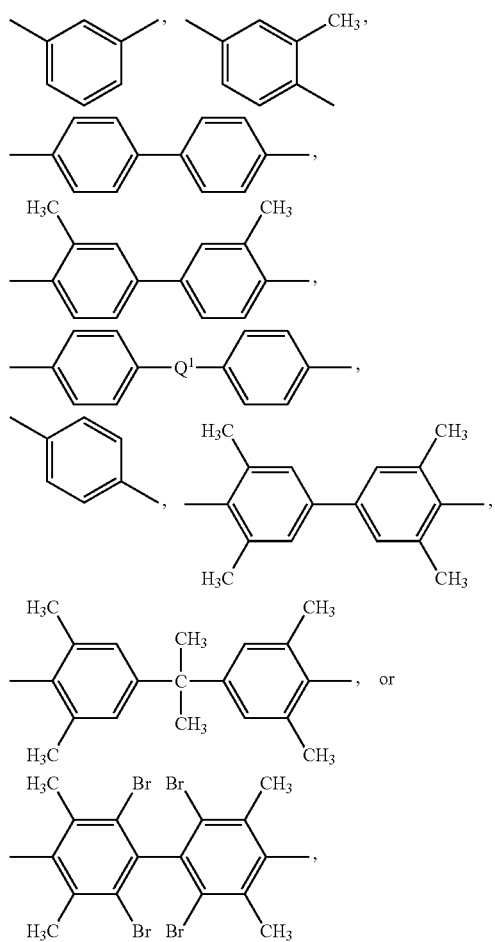

wherein $Q^1$ is selected from —O—, —S—, —C(O)—, —SO$_2$—, —SO—, and —C$_y$H$_{2y}$— wherein y is an integer from 1 to 5 and a halogenated derivative thereof; and Z is a divalent group of formula

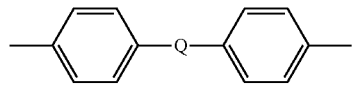

wherein Q is —O—, —S—, —C(O)—, —SO$_2$—, —SO—, or —C$_y$H$_{2y}$— wherein y is an integer from 1 to 5 and a halogenated derivative thereof Also disclosed is a polyetherimide composition wherein the bis(halophthalimide) composition comprises, based on the weight of the bis(halophthalimide) composition at least 15 wt. % of a 3,3'-bis(chlorophthalimide) of the formula

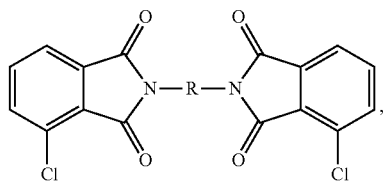

from more than 17 wt. % to less than 85 wt. % of a 4,3'-bis (chlorophthalimide) of the formula

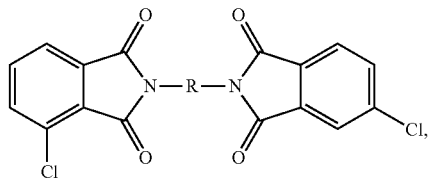

and
from more than 0 to less than 27 wt. % of a (4,4'-bis(chlorophthalimide) of the formula

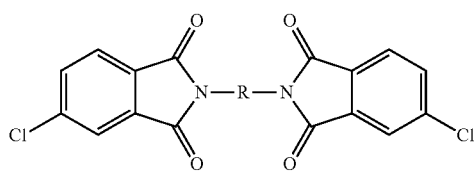

wherein R is as defined above.

In another embodiment, a method for the manufacture of a polyetherimide composition, the method comprising reacting: from 1.6 to 2.0 mole % excess of an alkali metal salt of a dihydroxy aromatic compound of the formula

MO—Z—OM wherein M is an alkali metal and Z is an aromatic $C_{6-24}$ monocyclic or polycyclic moiety optionally substituted with 1 to 6 $C_{1-8}$ alkyl groups, 1 to 8 halogen atoms, or a combination thereof; with a bis(halophthalimide) composition comprising, based on the weight of the bis(halophthalimide) composition, at least 15 wt. % of a 3,3'-bis(halophthalimide) of the formula

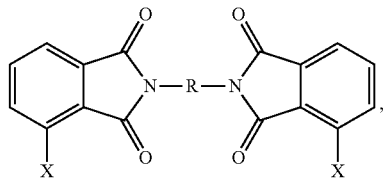

from more than 17 wt. % to less than 85 wt. % of a 4,3'-bis (halophthalimide) of the formula

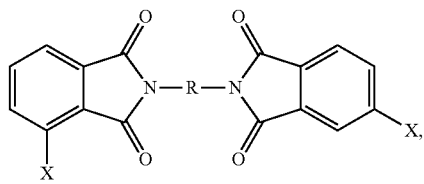

and
from more than 0 to less than 27 wt. % of a 4,4'-bis(halophthalimide) of the formula

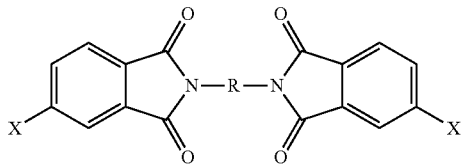

wherein each R is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

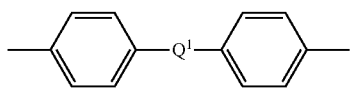

wherein $Q^1$ is selected from —O—, —S—, —C(O)—, —SO$_2$—, —SO—, and —C$_y$H$_{2y}$— wherein y is 1 to 5 and a halogenated derivative thereof, and each X is independently fluoro, chloro, bromo, or iodo; and adding from 2 to 4 mole % of a derivative of sodium phenoxide to the polyetherimide; to produce a polyetherimide of the formula

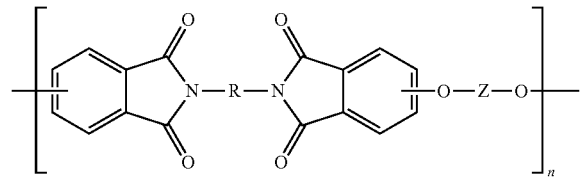

wherein n is greater than 1, each R is the same or different and is as defined above, each Z is the same or different, and is as defined above, and the divalent bonds between the —O—Z—O— group and the phenyl substituents are in the 3,3', 3,4', 4,3', and 4,4' positions; wherein the polyetherimide has: a Tg of greater than 220° C.; 20 to 35 wt. % solids; an Mw of at least 42,000 Daltons; a maximum chloride content of 900 ppm; a maximum of 700 ppm OH endgroup polymer functionality; and the low shear viscosity of the polyetherimide is at least 30% lower than a polyetherimide made from a bis(halophthalimide) composition comprising less than 10% of 4,3'-bis(halophthalimide.

Compositions comprising the above polyetherimides are disclosed.

A method of manufacture of the above compositions includes melt blending the compositions of the aforementioned polyetherimides.

Articles comprising the above compositions are also disclosed. In an embodiment, the article is selected from a reflector, an optical lens, a fiber optic connector, and an adhesive, specifically an adhesive for adhering a metal to a fluoropolymer such as poly(tetrafluoroethylene). In another embodiment, an article comprises (i) a polytetrafluoroethylene substrate having a first surface, (ii) a metal substrate having a second surface, and (iii) the polymer composition of the invention, situated between the polytetrafluoroethylene substrate and the metal substrate.

A method of forming the above articles includes shaping, extruding, blow molding, or injection molding the above compositions to form the article.

The invention is further illustrated by the Drawing, Detailed Description, and Examples.

BRIEF DESCRIPTION OF THE DRAWING

FIG. 1 summarizes the substantially less chlorine and OH substituents that compositions of our invention exhibited as compared to compositions used in Comparative Examples 2-5.

DETAILED DESCRIPTION OF THE INVENTION

The present inventors have discovered that precise control of the manner and timing of the addition of the bis(halophthalimide) regioisomers used in the preparation of polyetherimides by the halo-displacement process provides polyetherimides having a reduced content of residuals and byproducts, and in particular a halogen content of less than 900 ppm. Furthermore, the polyetherimides can have improved chemical and physical properties, including low shear viscosity.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed in this patent application. Because these ranges are continuous, they include every value between the minimum and maximum values. Unless expressly indicated otherwise, the various numerical ranges specified in this application are approximations. The endpoints of all ranges directed to the same composition or property are inclusive of the endpoint and independently combinable.

All molecular weights in this application refer to weight average molecular weights unless indicated otherwise and referenced to polystyrene standards. All such mentioned molecular weights are expressed in amu.

The terms "a" and "an" do not denote a limitation of quantity, but rather denote the presence of at least one of the referenced item. As used herein, "combination thereof" is inclusive of one or more of the recited elements, optionally together with a like element not recited. Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) can be combined in any suitable manner in the various embodiments.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The term "alkyl" includes both C$_{1-30}$ branched and straight chain, unsaturated aliphatic hydrocarbon groups having the specified number of carbon atoms, e.g., methyl, ethyl, n-propyl, i-propyl, n-butyl, s-butyl, t-butyl, n-pentyl, s-pentyl, n- and s-hexyl, n- and s-heptyl, and, n- and s-octyl. "Alkenyl" means a straight or branched chain, monovalent hydrocarbon group having at least one carbon-carbon double bond (e.g., ethenyl (—HC═CH₂)). "Alkoxy" means an alkyl group that is linked via an oxygen (i.e., alkyl-O—), for example, methoxy, ethoxy, and sec-butyloxy groups.

The term "aryl" means an aromatic moiety containing the specified number of carbon atoms, such as to phenyl, tropone, indanyl, or naphthyl. "Alkylene" means a straight or branched chain, saturated, divalent aliphatic hydrocarbon group (e.g., methylene (—CH₂—) or, propylene (—(CH₂)₃—)).

"Cycloalkylene" means a divalent cyclic alkylene group, —$C_nH_{2n-x}$, wherein x represents the number of hydrogens replaced by cyclization(s). "Cycloalkenyl" means a monovalent group having one or more rings and one or more carbon-carbon double bond(s) in the ring, wherein all ring members are carbon (e.g., cyclopentyl and cyclohexyl).

The prefix "halo" means a group or compound including one or more of a fluoro, chloro, bromo, iodo, and astatino substituent. A combination of different halo groups (e.g., bromo and fluoro) can be present. In an embodiment only chloro groups are present.

The prefix "hetero" means that the compound or group includes at least one ring that is a heteroatom (e.g., 1, 2, or 3 heteroatom(s)), wherein the heteroatom(s) is each independently N, O, S, Si, or P.

"Substituted" means that the compound or group is substituted with at least one (e.g., 1, 2, 3, or 4) substituent independently selected from, a $C_{1-9}$ alkoxy, a $C_{1-9}$ haloalkoxy, a nitro (—NO₂), a cyano (—CN), a $C_{1-6}$ alkyl sulfonyl (—S(═O)₂-alkyl), a $C_{6-12}$ aryl sulfonyl (—S(═O)₂-aryl) a thiol (—SH), a thiocyano (—SCN), a tosyl (CH₃C₆H₄SO₂—), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, or a $C_{3-12}$ heteroaryl instead of hydrogen, provided that the substituted atom's normal valence is not exceeded.

All ASTM tests are based on the 2003 edition of the Annual Book of ASTM Standards unless otherwise indicated.

The polyetherimides are of formula (1)

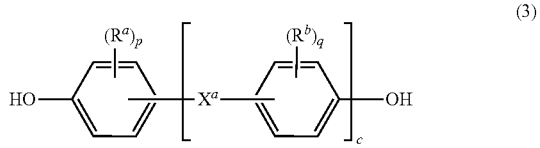
(1)

wherein n is greater than 1, for example, 10 to 1,000 or more, or more specifically 10 to 500.

The group R in formula (1) is a substituted or unsubstituted divalent organic group, such as a $C_{6-20}$ aromatic hydrocarbon group or a halogenated derivative thereof, a straight or branched chain $C_{2-20}$ alkylene group or halogenated derivatives thereof, a $C_{3-8}$ cycloalkylene group or halogenated derivative thereof, or a divalent group of formula (2)

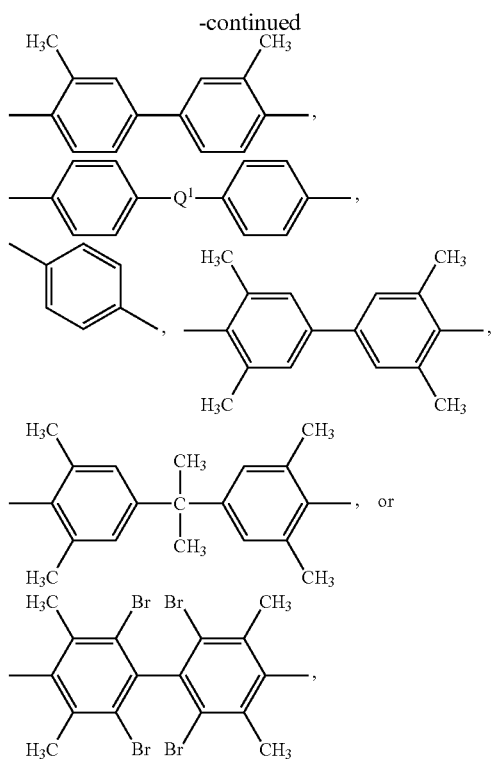

wherein $Q^1$ is —O—, —S—, —C(O)—, —SO₂—, —SO—, and —$C_yH_{2y}$— and a halogenated derivative thereof (which includes perfluoroalkylene groups) wherein y is an integer from 1 to 5. In a specific embodiment, R is m-phenylene or p-phenylene.

The group Z in formula (1) is also a substituted or unsubstituted divalent organic group, and can be an aromatic $C_{6-24}$ monocyclic or polycyclic moiety optionally substituted with 1 to 6 $C_{1-8}$ alkyl groups, 1 to 8 halogen atoms, or a combination thereof, provided that the valence of Z is not exceeded. Exemplary groups Z include groups derived from a dihydroxy compound of formula (3):

$$HO-\underset{(R^a)_p}{\underset{|}{\bigcirc}}-X^a-\underset{(R^b)_q}{\underset{|}{\bigcirc}}-OH \quad (3)$$

wherein $R^a$ and $R^b$ each represent a halogen atom or a monovalent hydrocarbon group and can be the same or different; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)₂—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of formulas (3a)

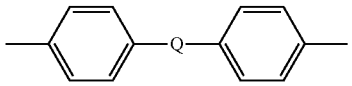
(3a)

wherein Q is —O—, —S—, —C(O)—, —$SO_2$—, —SO—, and —$C_yH_{2y}$— and a halogenated derivative thereof (including a perfluoroalkylene group) wherein y is an integer from 1 to 5. In a specific embodiment Z is derived from bisphenol A wherein Q is 2,2-isopropylidene.

In another specific embodiment, the polyetherimide comprises more than 1, specifically 10 to 1,000, or more specifically, 10 to 500 structural units, of formula (1) wherein R is a divalent group of formula (2) wherein $Q^1$ is —$C_yH_{2y}$— wherein y is an integer from 1 to 5 or a halogenated derivative thereof, and Z is a group of formula (3). In a specific embodiment, R is m-phenylene, p-arylene diphenylsulfone, or a combination thereof, and Z is 2,2-(4-phenylene)isopropylidene. For example, a polyetherimide sulfone comprises structural units of formula (1) wherein at least 50 mole % of the R groups are of formula (2) wherein $Q^1$ is —$SO_2$— and the remaining R groups are independently p-phenylene or m-phenylene or a combination comprising at least one of the foregoing; and Z is 2,2-(4-phenylene)isopropylidene.

The polyetherimide can be a copolymer, and combinations of polyetherimides can be used. In an embodiment, the polyetherimide optionally comprises additional structural imide units, for example, imide units of formula (4)

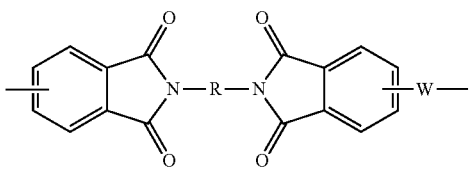
(4)

wherein R is as described in formula (1) and W is a linker of formulas (5)

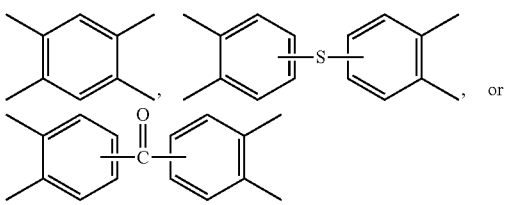
(5)

These additional structural imide units can be present in amounts ranging from 0 to 10 mole % of the total number of units, specifically 0 to 5 mole %, more specifically 0 to 2 mole %. In an embodiment no additional imide units are present in the polyetherimide.

The polyetherimides are prepared by the so-called "halo-displacement" or "chloro-displacement" method. In this method, a halophthalic anhydride of formula (6)

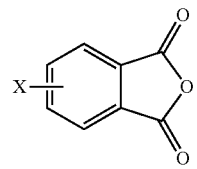
(6)

wherein X is a halogen, is condensed with an organic diamine of the formula (7)

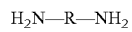
(7)

wherein R is as described in formula (1), to form a bis(halophthalimide) of formula (8)

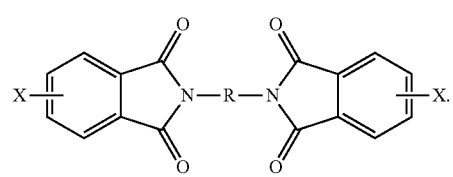
(8)

In an embodiment, X is a halogen, specifically fluoro, chloro, bromo, or iodo, more specifically chloro. A combination of different halogens can be used.

Illustrative examples of amine compounds of formula (7) include ethylenediamine, propylenediamine, trimethylenediamine, diethylenetriamine, triethylenetetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(b-amino-t-butyl) toluene, bis (p-b-amino-t-butylphenyl) ether, bis(p-b-methyl-o-aminophenyl)benzene, bis(p-b-methyl-o-aminopentyl)benzene, 1,3-diamino-4-isopropylbenzene, bis(4-aminophenyl) ether and 1,3-bis(3-aminopropyl)tetramethyldisiloxane. Combinations of these amines can be used. Illustrative examples of amine compounds of formula (7) containing sulfone groups include diamino diphenyl sulfone (DDS) and bis(aminophenoxy phenyl) sulfones (BAPS). Combinations comprising any of the foregoing amines can be used.

In a specific embodiment, diamine (7) is a meta-phenylene diamine (7a) or a para-phenylene diamine (7b)

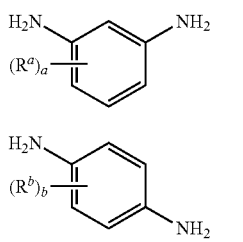

wherein $R^1$ and $R^2$ are each independently a halogen atom, nitro, cyano, $C_2$-$C_{20}$ aliphatic group, $C_2$-$C_{40}$ aromatic group, and a and b are each independently 0 to 4. Specific examples include meta-phenylenediamine (mDA), para-phenylenediamine (pDA), 2,4-diaminotoluene, 2,6-diaminotoluene, 2-methyl-4,6-diethyl-1,3-phenylenediamine, 5-methyl-4,6-diethyl-1,3-phenylenediamine, or 1,3-diamino-4-isopropylbenzene. Combinations comprising any of the foregoing amines can be used.

Condensation of halophthalic anhydride (6) and amine (7) (imidization) can be conducted in the absence or presence of a catalyst. Exemplary phase transfer catalysts for imidization include sodium phenyl phosphinate (SPP), acetic acid, hexaethylguanidinium chloride, benzoic acid, phthalic acid, or substituted derivatives thereof. In an embodiment, sodium phenyl phosphinate is used as the imidization catalyst. The catalyst, if used, is present in an amount effective to accelerate the reaction, for example, about 0.1-0.3 wt. % based on the weight of diamine.

An end-capping agent selected from derivatives of sodium phenoxide is added, in an effective amount, for example, from 2 to 4 mole % based upon the polymer. Sodium phenoxide derivatives include sodium phenol and sodium para-cumyl phenol.

The reaction is generally conducted in the presence of a relatively non-polar solvent, preferably with a boiling point above about 100° C., specifically above about 150° C., for example, o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned.

The bis(halophthalimide)s (8) are generally prepared at least 110° C., specifically 150° to 275° C., more specifically 175° to 225° C. At temperatures below 110° C., reaction rates can be too slow for economical operation. Atmospheric or super-atmospheric pressures can be used, for example, up to 5 atmospheres, to facilitate the use of high temperatures without causing solvent to be lost by evaporation.

The solvent, diamine (7), and halophthalic anhydride (6) can be combined in amounts such that the total solids content during the reaction to form bis(halophthalimide) (8) does not exceed about 40 wt. %, 25 wt. %, or about 17 wt. %. "Total solids content" expresses the proportion of the reactants as a percentage of the total weight comprising liquids present in the reaction at any given time.

A molar ratio of halophthalic anhydride (6) to diamine (7) of 1.98:1 to 2.04:1, specifically 2:1 is used. While other ratios can be employed, a slight excess of anhydride or diamine can be desirable. A proper stoichiometric balance between halophthalic anhydride (6) and diamine (7) is maintained to prevent undesirable by-products that can limit the molecular weight of the polymer, and/or result in polymers with amine end groups. Accordingly, in an embodiment, imidization proceeds adding diamine (7) to a mixture of halophthalic anhydride (6) and solvent to form a reaction mixture having a targeted initial molar ratio of halophthalic anhydride to diamine; heating the reaction mixture to a temperature of at least 100° C. (optionally in the presence of an imidization catalyst); analyzing the molar ratio of the heated reaction mixture to determine the actual initial molar ratio of halophthalic anhydride (6) to diamine (7); and, if necessary, adding halophthalic anhydride (6) or diamine (7) to the analyzed reaction mixture to adjust the molar ratio of halophthalic anhydride (6) to diamine (7) to 2.01 to 2.3.

To produce a mixture of isomers in the desired range, the 4-halophthalic and 3-halophthalic anhydride are added in relative ratios of for example, 75:25 to 25:75; 60:40 to 40:60; or approximately 50:50.

After imidization, the halogen group X of bis(halophthalimide) (8)

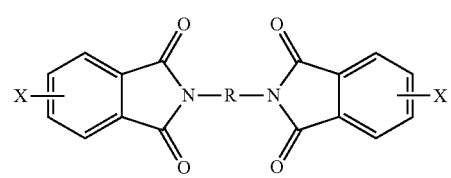

is displaced by reaction with an alkali metal salt of a dihydroxy aromatic compound of formula (9)

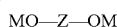

wherein M is an alkali metal and Z is as described in formula (1), to provide the polyetherimide of formula (1)

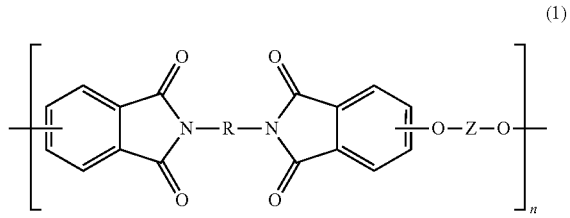

wherein n, R, and Z are as defined above.

The alkali metal M can be any alkali metal, and is typically potassium or sodium. The alkali metal salt can be obtained by reaction of the metal with an aromatic $C_{6-24}$ monocyclic or polycyclic dihydroxy compound optionally substituted with 1 to 6 $C_{1-8}$ alkyl groups, 1 to 8 halogen atoms, or a combination thereof, for example, a compound of formula (3), more specifically a dihydroxy compound corresponding to one of the groups of formulas (3a), and still more specifically a bisphenol compound of formula (10):

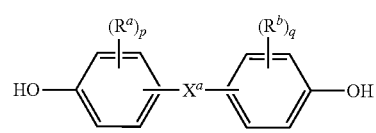

wherein $R^a$, $R^b$, and $X^a$ are as described in formula (3). For example, 2,2-bis(4-hydroxyphenyl) propane ("bisphenol A" or "BPA") can be used.

Polymerization by reaction of bis(halophthalimide) (8) with alkali metal salt (9) can be conducted in the presence or absence of a phase transfer catalyst that is substantially stable under the reaction conditions used, in particular temperature. Exemplary phase transfer catalysts for polymerization include hexaalkylguanidinium and α,ω-bis(pentaalkylguanidinium)alkane salts. Both types of salts can be referred to herein as "guanidinium salts."

Polymerization is generally conducted in the presence of a relatively non-polar solvent, preferably with a boiling point above about 100° C., specifically above about 150° C., for example, o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned. Alternatively, a polar aprotic solvent can be used, illustrative examples of which include dimethylformamide (DMF), dimethylacetamide (DMAc), dimethylsulfoxide (DMSO), and N-methylpyrrolidinone (NMP). A combination comprising at least one of the foregoing solvents can be used.

Polymerization can be conducted at a temperature of at least 110° C., specifically 150° to 275° C., more specifically 175° to 225° C. At temperatures below 110° C., reaction rates can be too slow for economical operation. Atmospheric or super-atmospheric pressures can be used, for example, up to 5 atmospheres, to facilitate the use of high temperatures without causing solvent to be lost by evaporation.

In an embodiment, alkali metal salt (9) is added to the organic solvent and the water is removed from the mixture, for example, as its azeotrope. The bis(halophthalimide) (8) is then added and water removed from the mixture, for example, as its azeotrope, followed by addition of a catalyst in a pre-dried solution in organic solvent. Water removal from the system can be accomplished in either batch, semi-continuous or continuous processes using means known in the art such as a distillation column in conjunction with one or more reactors. In an embodiment, a mixture of water and non-polar organic liquid distilling from a reactor is sent to a distillation column where water is taken off overhead and solvent is recycled back into the reactor at a rate to maintain or increase the desired solids concentration. Other methods for water removal include passing the condensed distillate through a drying bed for chemical or physical adsorption of water.

The molar ratio of the bis(halophthalimide) (8) to the alkali metal salt (9) provides a 1.6 to 2.0 mole % excess of the alkali metal salt of a dihydroxy aromatic compound. A solids content of the bis(halophthalimide) (8) in the polymerization can be 15 to 60 wt. %, based on the total weight of the polymerization mixture.

Thus, a method for the manufacture of the polyetherimides from the bis(halophthalimide) composition comprises reacting, in the presence of a catalytically active amount of a phase transfer catalyst, the alkali metal salt (9) with a bis(halophthalimide) (8). It has been discovered by the inventors hereof that desirable properties of the polyetherimide can be obtained by careful selection of the regioisomers of the bis(halophthalimide)s (8) used to manufacture the polyetherimides. In particular, the bis(halophthalimide)s (8) can be formed from the 3-halophthalic anhydride (6a) and/or the 4-halophthalic anhydride (6b)

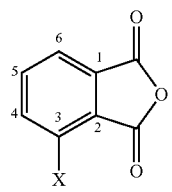

(6a)

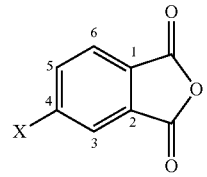

(6b)

to provide the 3,3'-bis(halophthalimide) (8a), the 3,4'-bis(halophthalimide) (8b), and/or the 4,4'-bis(halophthalimide) (8c)

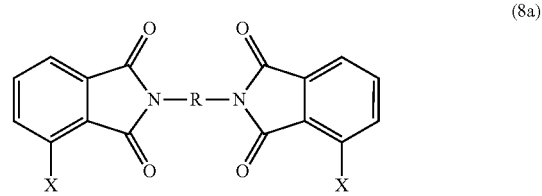

(8a)

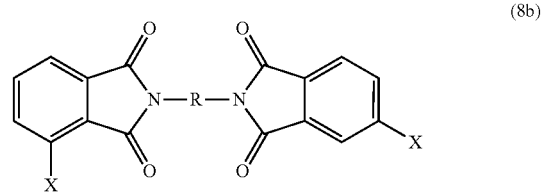

(8b)

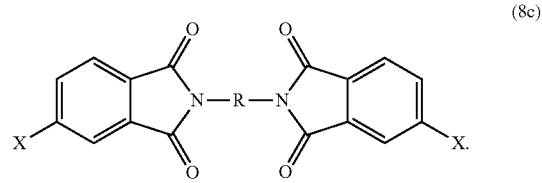

(8c)

As can be seen from formula (8b), when R is symmetrical (e.g., a 1,3-phenylene or 1,4-phenylene) the 3,4'- and 4,3' isomers are the same, but when R is not symmetrical (e.g., 1-methyl-2,3-phenylene) the 3,4' and 4,3' regioisomers are not the same. Reference to the 3,4' isomer herein and in the claims specifically includes the 4,3' isomer irrespective of whether R is symmetrical. In a specific embodiment, a combination of 3-chlorophthalic anhydride (3-CIPA), 4-chlorophthalic anhydride (4-CIPA) and a diamine (7) (e.g., meta-phenylene diamine) are reacted to produce the bis(chlorophthalimide) (CIPAMI) composition as a mixture of the 3,3'-bis(chlorophthalimide) (3,3-CIPAMI) (1,3-bis[N-(3-chlorophthalimido)]benzene), the 3,4'-bis(chlorophthalimide) (3,4'-CIPAMI) (1,3-bis[N-(3-chlorophthalimido,4-chlorophthalimido)]benzene), and the 4,4'-bis(chlorophthalimide) (4,4'-CIPAMI) (1,3-bis[N-(4-chlorophthalimido)]benzene).

Without being bound by theory, it is believed that the solubility of the 3,4'-bis(halophthalimide) (8b), (e.g., the 3,4-CIPAMI isomer) is about ten-fold greater than the 3,3-bis(halophthalimide) and the 4,4'-bis(halophthalimide) (including the 3,3'- and 4,4'-CIPAMI isomers).

Thus, the polyetherimides are manufactured from a bis(halophthalimide) composition, specifically the bis(chlorophthalimide) composition, comprising the 3,3'-bis(halophthalimide) (8a), specifically 3,3'-CIPAMI, in an amount of at least 15 wt. %, specifically 15 to less than 85 wt. %, more specifically 17 to 80 wt. %, or 19 to 75 wt. %, based on the total weight of the bis(halophthalimide) composition. In another embodiment, the bis(halophthalimide) composition comprises 15 to less than 53 wt. %, specifically 17 to 51 wt. %, more specifically 19 to 49 wt. % of 3,3'-bis(halophthalimide) (8a), specifically 3,3'-CIPAMI, based on the weight of the bis(halophthalimide) composition.

The bis(halophthalimide) composition, specifically the bis(chlorophthalimide) composition, also further comprises the 4,3'-bis(halophthalimide) (8b), specifically 3,4'-CIPAMI, in an amount of more than 10 wt. %, specifically more than 10 wt. % to less than 85 wt. %, or more than 17 wt. % to less than 85 wt. %, or 18 to 84 wt. %, or 19 to 82 wt. %, or 25 to 80 wt. %, or 30 to 78 wt. %, based on the total weight of the bis(halophthalimide) composition. Alternatively, the bis(halophthalimide) composition comprises 50 to 85 wt. %, or 68 to 85 wt. % of 4,3'-bis(halophthalimide) (8b), specifically 3,4'-CIPAMI, based on the total weight of the bis(halophthalimide) composition. In another embodiment, the bis(halophthalimide) composition comprises more than 47 to less than 85 wt. %, or 49 to 80 wt. %, or 51 to 75 wt. % of the 4,3'-bis(halophthalimide) of formula (8b), specifically 3,4'-CIPAMI, based on the weight of the bis(halophthalimide) composition.

Also, the bis(halophthalimide) composition, specifically the bis(chlorophthalimide) composition, comprises the 4,4'-bis(halophthalimide) (8c), specifically 4,4'-CIPAMI, in an amount of from more than 0 to less than 27 wt. %, specifically 1 to 26 wt. %, or 2 to 24 wt. %, or 3 to 20 wt. %, based on the weight of the bis(halophthalimide) composition.

Thus, in a method for the manufacture of the polyetherimides, a first portion of the alkali metal salt of the dihydroxy aromatic compound is reacted with the bis(halophthalimide) composition to form a first polyetherimide having a first molecular weight; and a second portion of the alkali metal salt of the dihydroxy aromatic compound is added to the first polyetherimide to form a second polyetherimide having a second molecular weight higher than the first molecular weight. In another embodiment, a third portion of the alkali metal salt of the dihydroxy aromatic compound is added to the second polyetherimide to form a third polyetherimide having a third molecular weight higher than the second molecular weight. In still another embodiment, a fourth portion of the alkali metal salt of the dihydroxy aromatic compound is added to the third polyetherimide to form a fourth polyetherimide having a fourth molecular weight higher than the third molecular weight. The reaction mixture containing this product is then subjected to 1 to 5, specifically 1 to 3, or 1 to 2 corrections by the addition of additional alkali metal salt, in order to produce a polymer having an Mw of 50,000 to 60,000 amu.

The polyetherimides manufactured using the above-described bis(halophthalimide) composition have the —O—Z—O— groups in the polyetherimide in the 3,3', 3,4', 4,3', and 4,4' positions in the same or substantially the same ratio as in the bis(halophthalimide) compositions. In an embodiment, the polyetherimide is of formula (1)

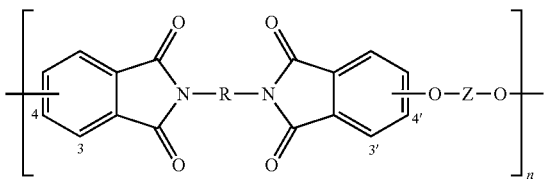

wherein n, R, and Z are as defined above. In addition, based on the total mole percent of the —O—Z—O— groups in the polyetherimide, the polyetherimides have more than 0 to less than 15 mole percent of the —O—Z—O— groups in the 3,3' position, more than 17 less than 85 mole percent of the —O—Z—O— groups in the 3,4', and 4',3 positions, specifically more than 47 wt. % to less than 85 wt. % of the —O—Z—O— groups in the 3,4', and 4',3 positions, and from more than 0 to less than 27 mole percent of the divalent bonds of the —O—Z—O— groups in the 4,4' position. In an embodiment, the polyetherimide has from 15 to less than 85 mol % of the of the —O—Z—O— groups in the 3,3' position, from more than 47 to less than 85 mol % of the O—Z—O— groups in the 4,3' and 3,4' positions, and from more than 0 to less than 27 mol % of the O—Z—O— groups in the 4,4' position. In another embodiment, based on the total mole percent of the —O—Z—O— groups in the polyetherimide, the polyetherimide has at least 15 mol % the divalent bonds of the —O—Z—O— groups are in the 3,3' position, more than 10 mol % of the —O—Z—O— groups are in the 3,4', and 4',3 positions, and less than 27 mol % of the —O—Z—O— groups are 4,4' position. Other mole percents, reflective of the weight percents in the bis(halophthalimide) compositions disclosed herein, can be used. Of course, these polyetherimides can have any one or more of the properties and characteristics described herein.

The polyetherimides manufactured using the above-described bis(halophthalimide) composition can comprise, based on parts by weight of the polyetherimide, less than 100 parts per million (ppm), specifically less than 80 ppm, more specifically less than 60 ppm each of the 3,3'-bis(halophthalimide), the 4,3'-bis(halophthalimide), and the 4,4'-bis(halophthalimide). In addition, the polyetherimide can comprise, based on parts of the polyetherimide, less than 100 ppm, specifically less than 80 ppm, more specifically less than 60 ppm of a halo(bisphthalimide) of the formula

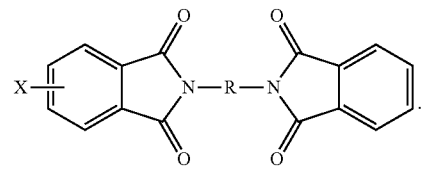

In addition, the polyetherimide can comprise, based on parts of the polyetherimide, less than 100 ppm, specifically less than 80 ppm, more specifically less than 60 ppm of a bisphthalimide of the formula

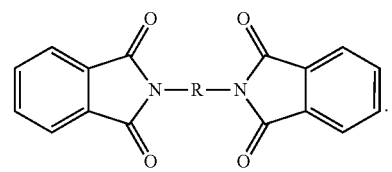

Also, the polyetherimide can comprise, based on parts of the polyetherimide, less than 200 ppm, specifically less than 180 ppm, more specifically less than 160 ppm of a total of the 3,3'-bis(halophthalimide), the 4,3'-bis(halophthalimide), the 4,4'-bis(halophthalimide), and the halo(bisphthalimide).

The polyetherimides can have a weight average molecular weight (Mw) of 5,000 to 100,000 grams per mole (g/mole) as measured by gel permeation chromatography (GPC). In some embodiments, the Mw can be 10,000 to 80,000. The molecular weights as used herein refer to the polystyrene standard weight averaged molecular weight (Mw).

The polyetherimides can have an intrinsic viscosity greater than or equal to 0.2 deciliters per gram (dl/g) as measured in m-cresol at 25° C. Within this range the intrinsic viscosity can be 0.35 to 1.0 dl/g, as measured in m-cresol at 25° C.

The polyetherimides can have a glass transition temperature of greater than 180° C., specifically of 200° to 315° C., more specifically as measured using differential scanning calorimetry (DSC) per ASTM test D3418. In an embodiment the polyetherimide has a glass transition temperature of 220° to 240° C.

The compositions can further optionally comprise a reinforcing filler, for example, a flat, plate-like, and/or fibrous filler. Typically, the flat, plate-like filler has a length and width at least ten times greater than its thickness, where the thickness is from 1 to 1000 micrometers (µm). Exemplary reinforcing fillers of this type include glass flakes, mica, flaked silicon carbide, aluminum diboride, aluminum flakes, and steel flakes; wollastonite comprising surface-treated wollastonite; calcium carbonate comprising chalk, limestone, marble and synthetic, precipitated calcium carbonates, generally in the form of a ground particulates; talc, comprising fibrous, modular, needle shaped, and lamellar talc; kaolin, comprising hard, soft, calcined kaolin, and kaolin comprising various coatings known in the art to facilitate compatibility with the polymeric matrix resin; mica; and feldspar.

Exemplary reinforcing fillers also include fibrous fillers such as short inorganic fibers, natural mineral fibrous fillers, single crystal fibers, glass fibers, ceramic fibers, and organic reinforcing fibrous fillers. Short inorganic fibers include, borosilicate glass, carbon fibers, and those derived from blends comprising at least one of aluminum silicates, aluminum oxides, magnesium oxides, and calcium sulfate hemihydrate. Single crystal fibers or "whiskers" include silicon carbide, alumina, boron carbide, iron, nickel, and copper single crystal fibers. Glass fibers, comprising glass fibers such as E, ECR, S, and NE glasses and quartz, and the like can also be used.

Such reinforcing fillers can be provided in the form of monofilament or multifilament fibers and can be used either alone or in combination with other types of fiber, through, for example, co-weaving or core/sheath, side-by-side, orange-type or matrix and fibril constructions, or by other methods known to one skilled in the art of fiber manufacture. Typical cowoven structures include glass fiber-carbon fiber, carbon fiber-aromatic polyimide (aramid) fiber, and aromatic polyimide fiber-glass fiber. Fibrous fillers can be supplied in the form of, for example, rovings, woven fibrous reinforcements, such as 0-90 degree fabrics, non-woven fibrous reinforcements such as continuous strand mat, chopped strand mat, tissues, papers and felts and 3-dimensionally woven reinforcements, performs and braids.

The reinforcing fibers can have a diameter of 5 to 25 micrometers, specifically diameters of 9 to 15 micrometers. In preparing molding compositions it is convenient to use reinforcing fibers such as fiberglass in the form of chopped strands of from 3 millimeters to 15 millimeters long. In articles molded from these compositions, on the other hand, shorter lengths will typically be encountered because during compounding considerable fragmentation can occur. Combinations of rigid fibrous fillers with flat, plate-like fillers can be used, for example, to reduce warp of a molded article.

In some applications, it can be desirable to treat the surface of the filler with a chemical coupling agent to improve adhesion to a thermoplastic resin in the composition. Examples of useful coupling agents are alkoxy silanes and alkoxy zirconates Amino, epoxy, amide, or thio functional alkoxy silanes are especially useful. Fiber coatings with high thermal stability are preferred to prevent decomposition of the coating, which could result in foaming or gas generation during processing at the high melt temperatures required to form the compositions into molded parts.

The amount of reinforcing filler used in the polyetherimide compositions can vary widely, and is that amount effective to provide the desired physical properties and flame resistance. In some instances the reinforcing filler is present in an amount from more than 10 to 60 wt. %, more specifically 15 to 40 wt. %, and even more specifically 20 to 35 wt. %, each based on the total weight of the composition.

The polyetherimide compositions can optionally further comprise one or more other types of particulate fillers. Exemplary particulate fillers include silica powder, such as fused silica and crystalline silica; boron-nitride powder and boron-silicate powders; alumina, and magnesium oxide (or magnesia); silicate spheres; flue dust; cenospheres; aluminosilicate (armospheres); natural silica sand; quartz; quartzite; perlite; tripoli; diatomaceous earth; synthetic silica; and combinations thereof. All of the above fillers can be surface treated with silanes to improve adhesion and dispersion with the polymeric matrix resin. When present, the amount of additional particulate filler in the polyetherimide composition can vary widely, and is that amount effective to provide the desired physical properties and flame resistance. In some instances the particulate filler is present in an amount from 1 to 80 wt. %, specifically 5 to 30 wt. %, more specifically 5 to 20 wt. %, each based on the total weight of the composition.

The polyetherimide compositions can include various additives ordinarily incorporated into polymer compositions of this type, with the proviso that any additive is selected so as to not significantly adversely affect the desired properties of the composition. Exemplary additives include catalysts (for example, to facilitate reaction between an impact modifier and the polyester), antioxidants, thermal stabilizers, light stabilizers, ultraviolet light (UV) absorbing additives, quenchers, plasticizers, lubricants, mold release agents, antistatic agents, visual effect additives such as dyes, pigments, and light effect additives, flame resistances, anti-drip agents, and radiation stabilizers. Combinations of additives can be used. The foregoing additives (except any fillers) are generally present in an amount from 0.005 to 20 wt. %, specifically 0.01 to 10 wt. %, based on the total weight of the composition.

Suitable antioxidants can be compounds such as phosphites, phosphonites and hindered phenols or mixtures thereof. Phosphorus-containing stabilizers comprising triaryl phosphites and aryl phosphonates are useful additives. Difunctional phosphorus containing compounds can also be unseeded. Preferred stabilizers can have a molecular weight greater than or equal to 300. Some exemplary compounds are tris-di-tert-butylphenyl phosphite available from Ciba Chemical Co. as IRGAPHOS 168 and bis (2,4-dicumylphenyl) pentaerythritol diphosphite available commercially from Dover Chemical Co. as DOVERPHOS S-9228.

Examples of phosphites and phosphonites include: triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxy pentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butyl-phenyl) 4,4'-biphenylene diphosphonite, bis(2,4-di-tert-butyl-6- methylphenyl) methyl phosphite, bis(2,4-di-tert-butyl-6-methylphenyl) ethyl phosphite, 2,2',2''-nitrilo[triethyl tris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite and 5-butyl-5-ethyl-2-(2,4,6-tri-tert-butylphenoxy)-1,3,2-dioxaphosphirane.

Combinations comprising more than one organophosphorous compound are contemplated. When used in combination the organophosphorous compounds can be of the same type or different types. For example, a combination can comprise two phosphites or a combination can comprise a phosphite and a phosphonite. In some embodiments, phosphorus-containing stabilizers with a molecular weight greater than or equal to 300 are useful. Phosphorus-containing stabilizers, for example, an aryl phosphite, may be present in the composition in an amount from 0.005 to 3 wt. %, specifically 0.01 to 1.0 wt. %, based on total weight of the composition.

Hindered phenols can also be used as antioxidants, for example, alkylated monophenols, and alkylated bisphenols or poly phenols. Exemplary alkylated monophenols include 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(alpha-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonyl phenols which are linear or branched in the side chains, for example, 2,6-di-nonyl-4-methylphenol; 2,4-dimethyl-6-(1'-methylundec-1'-yl)phenol; 2,4-dimethyl-6-(1'-methylheptadec-1'-yl)phenol; 2,4-dimethyl-6-(1'-methyltridec-1'-yl)phenol and mixtures thereof. Exemplary alkylidene bisphenols include 2,2'-methylenebis(6-tert-butyl-4-methylphenol), 2,2'-methylenebis(6-tert-butyl-4-ethylphenol), 2,2'-methylenebis[4-methyl-6-(alpha-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(alpha-methylbenzyl)-4-nonylphenol], 2,2'-methylenebis[6-(alpha, alpha-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane and mixtures thereof.

The hindered phenol compound can have a molecular weight of greater than or equal to 300 g/mole. The high molecular weight can help retain the hindered phenol moiety in the polymer melt at high processing temperatures, for example, greater than or equal to 300° C. Hindered phenol stabilizers, are usually present in the composition in an amount from 0.005 to 2 wt. %, specifically 0.01 to 1.0 wt. %, based on total weight of the composition.

Examples of mold release agents include both aliphatic and aromatic carboxylic acids and their alkyl esters, for example, stearic acid, behenic acid, pentaerythritol tetrastearate, glycerin tristearate, and ethylene glycol distearate. Polyolefins such as high-density polyethylene, linear low-density polyethylene, low-density polyethylene and similar polyolefin homopolymers and copolymers can also be used as mold release agents. Mold release agents are typically present in the composition at 0.05 to 10 wt. %, based on total weight of the composition, specifically 0.1 to 5 wt. %. Preferred mold release agents will have high molecular weight, typically greater than 300, to prevent loss of the release agent from the molten polymer mixture during melt processing.

In particular, an optional polyolefin can be added to modify the chemical resistance characteristics and mold release characteristics of the composition. Homopolymers such as polyethylene, polypropylene, polybutene can be used either separately or in combination. Polyethylene can be added as high-density polyethylene (HDPE), low-density polyethylene (LDPE) or branched polyethylene. Polyolefins can also be used in copolymeric form with compounds containing carbonic acid radicals such as maleic acid or citric acid or their anhydrides, acid compounds containing acrylic acid radicals such as acrylic acid ester, and the like, as well as combinations comprising at least one of the foregoing. When present, the polyolefin, in particular HDPET, is used in an amount from more than 0 to 10 wt. %, specifically 0.1 to 8 wt. %, more specifically from 0.5 to 5 wt. %, all based on the total weight of the composition.

In some embodiments, the compositions can further include at least one additional polymer. Examples of such additional polymers include and are not limited to PPSU (polyphenylene sulfone), polyetherimides, PSU (polysulfone), PPET (polyphenylene ether), PFA (perfluoroalkoxy alkane), MFA (co-polymer of TFE tetrafluoroethylene and PFVE perfluorinated vinyl ether), FEP (fluorinated ethylene propylene polymers), PPS (poly(phenylene sulfide), PTFE (polytetrafluoroethylene), PA (polyamide), PBI (polybenzimidizole) and PAI (poly(amide-imide)), poly(ether sulfone), poly(aryl sulfone), polyphenylenes, polybenzoxazoles, polybenzthiazoles, as well as blends and co-polymers thereof. When present, the polymer is used in an amount from more than 0 to 20 wt. %, specifically 0.1 to 15 wt. %, more specifically from 0.5 to 10 wt. %, all based on the total weight of the composition. In an embodiment, no polymer other than the polyetherimide as described herein is present in the composition.

Colorants such as pigment and/or dye additives can also optionally be present. Useful pigments can include, for example, inorganic pigments such as metal oxides and mixed metal oxides such as zinc oxide, titanium dioxide, iron oxides, or the like; sulfides such as zinc sulfides, or the like; aluminates; sodium sulfo-silicates sulfates, chromates, or the like; carbon blacks; zinc ferrites; ultramarine blue; organic pigments such as azos, di-azos, quinacridones, perylenes, naphthalene tetracarboxylic acids, flavanthrones, isoindolinones, tetrachloroisoindolinones, anthraquinones, enthrones, dioxazines, phthalocyanines, and azo lakes; Pigment Red 101, Pigment Red 122, Pigment Red 149, Pigment Red 177, Pigment Red 179, Pigment Red 202, Pigment Violet 29, Pigment Blue 15, Pigment Blue 60, Pigment Green 7, Pigment Yellow 119, Pigment Yellow 147, Pigment Yellow 150, and Pigment Brown 24; or combinations comprising at least one of the foregoing pigments. Pigments are generally used in amount from 0 to 10 wt. %, specifically 0 to 5 wt. %, based on the total weight of the composition. In some instances, where improved impact is desired, pigments such as titanium dioxide will have a mean particle size of less than 5 μm.

The composition can also optionally include a fluoropolymer in an effective amount to provide anti-drip or other beneficial properties to the resin composition. In one instance, the fluoropolymer is present in an amount 0.01 to 5.0 wt. % of the composition. Examples of suitable fluoropolymers and methods for making such fluoropolymers are set forth, for example, in U.S. Pat. Nos. 3,671,487, 3,723,373, and 3,383,092. Suitable fluoropolymers include homopolymers and copolymers that comprise structural units derived from one or more fluorinated alpha-olefin monomers, for example, $CF_2=CF_2$, $CHF=CF_2$, $CH_2=CF_2$ and $CH_2=CHF$ and fluoro propylenes such as, for example, $CF_3CF=CF_2$, $CF_3CF=CHF$, $CF_3CH=CF_2$, $CF_3CH=CH_2$, $CF_3CF=CHF$, $CHF_2CH=CHF$ and $CF_3CF=CH_2$.

Copolymers comprising structural units derived from two or more fluorinated alpha-olefin monomers can also be used, for example, poly(tetrafluoroethylene-hexafluoroethylene), as well as copolymers comprising structural units derived from one or more fluorinated monomers and one or more non-fluorinated monoethylenically unsaturated monomers that are copolymerizable with the fluorinated monomers such as poly(tetrafluoroethylene-ethylene-propylene) copolymers. Suitable non-fluorinated monoethylenically unsaturated monomers include for example, alpha-olefin monomers such as ethylene, propylene, butene, acrylate monomers such as, methyl methacrylate, butyl acrylate, and the like, with poly(tetrafluoroethylene) homopolymer (PTFE) preferred.

The fluoropolymer can be pre-blended in some manner with a polymer such as an aromatic polycarbonate or polyetherimide resin. For example, an aqueous dispersion of fluoropolymer and a polycarbonate resin can be steam precipitated to form a fluoropolymer concentrate for use as a drip inhibitor additive in thermoplastic resin compositions, as disclosed, for example, in U.S. Pat. No. 5,521,230. Alternatively, the fluoropolymer can be encapsulated.

In some instances, it is desired to have polyetherimide compositions that are essentially free of bromine and chlorine. "Essentially free" of bromine and chlorine means that the composition has less than 3 wt. % of bromine and chlorine, and, in other embodiments, less than 1 wt. % bromine and chlorine by weight of the composition. In other embodiments, the composition is halogen free. "Halogen free" is defined as having a halogen content (total amount of fluorine, bromine, chlorine and iodine) of less than or equal to 1000 parts by weight of halogen per million parts by weight of the total composition (ppm). The amount of halogen can be determined by ordinary chemical analysis such as atomic absorption.

The polyetherimide compositions can be prepared by blending the ingredients under conditions for the formation of an intimate blend. Such conditions often include melt mixing in single or twin screw type extruders, mixing bowl, or similar mixing devices that can apply a shear to the components. Twin-screw extruders are often preferred due to their more intensive mixing capability and self-wiping capability, over single screw extruders. It is often advantageous to apply a vacuum to the blend through at least one vent port in the extruder to remove volatile impurities in the composition. Often it is advantageous to dry the polyetherimide polymers prior to melting. The melt processing is often done at 290° to 370° C. to avoid excessive polymer degradation while still allowing sufficient melting to get an intimate polymer mixture free of any unbelted components. The polymer blend can also be melt filtered using a 40 to 100 micrometer candle or screen filter to remove undesirable black specks or other heterogeneous contaminants.

In an exemplary process, the various components are placed into an extrusion compounder to produce a continuous strand that is cooled and then chopped into pellets. In another procedure, the components are mixed by dry blending, and then fluxed on a mill and comminuted, or extruded and chopped. The composition and any optional components can also be mixed and directly molded, e.g., by injection or transfer molding techniques. Preferably, all of the components are freed from as much water as possible. In addition, compounding is carried out to ensure that the residence time in the machine is short; the temperature is carefully controlled; the friction heat is utilized; and an intimate blend between the components is obtained.

The composition can then be molded in any equipment conventionally used for thermoplastic compositions, such as a Newbury or van Dorn type injection-molding machine with conventional cylinder temperatures, at 320° to 420° C., and conventional mold temperatures at 100° to 170° C.

Further, when the bis(halophthalimide) composition comprises from more than 47 wt. % to less than 85 wt. % of the 4,3'-bis(halophthalimide), the polyetherimide comprises, based on parts of the polyetherimide, less than 100 parts per million each of the 3,3'-bis(halophthalimide), the 4,3'-bis(halophthalimide), and the 4,4'-bis(halophthalimide), less than 100 parts per million of a monohalo(bisphthalimide) of the formula

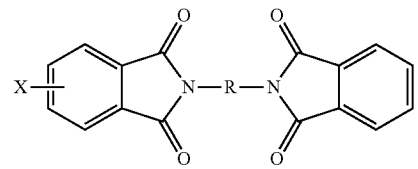

less than 100 parts per million of an unsubstituted bisphthalimide of the formula

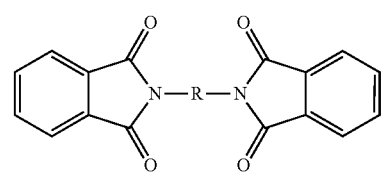

and less than 200 parts per million of a total of the 3,3'-bis(halophthalimide), the 4,3'-bis(halophthalimide), the 4,4'-bis(halophthalimide), and the monohalo(bisphthalimide). In a further embodiment, each halo group is a chloro group. In a still further embodiment, when X is a halide, more specifically a chloride, the polyetherimide comprises less than 2000 parts per million of halide (specifically chloride) ion; and less than 1.5 wt. % of a cyclic adduct of the dihydroxy aromatic compound and the bis(halophthalimide).

Also disclosed are articles comprising the above-described polyetherimide compositions. The article can be a sheet, film, multilayer sheet, multilayer film, molded part, extruded profile, coated part, or fiber. Also, the article can be a molded part having a thickness from 0.1 to 100 mm, specifically 1 to 10 mm, more specifically 1 to 5 mm.

The polyetherimide compositions can be formed into articles by any number of methods, for example, shaping, extruding (including profile extrusion), thermoforming, or molding, including injection molding, compression molding, gas assist molding, structural foam molding, and blow molding. In an embodiment, a method of forming an article comprises shaping, extruding, blow molding, or injection molding the composition to form the article. Polyetherimide compositions can also be formed into articles using thermoplastic processes such as film and sheet extrusion, for example, melt casting, blown film extrusion and calendaring. Co-extrusion and lamination processes can be used to form composite multi-layer films or sheets.

Examples of applications include food service, medical, lighting, lenses, sight glasses, windows, enclosures, safety shields, and the like. The high melt flow allows the composition to be molded into intricate parts with complex shapes and/or thin sections and long flow lengths. Examples of other articles include, but are not limited to, cookware, medical devices, trays, plates, handles, helmets, animal cages, electrical connectors, enclosures for electrical equipment, engine parts, automotive engine parts, lighting sockets and reflectors, electric motor parts, power distribution equipment, communication equipment, computers and the like, comprising devices that have been molded in snap fit connectors. The polyetherimide compositions can also be made into film and sheet as well as compositions of laminate systems. Other articles include, for example, fibers, sheets, films, multilayer sheets, multilayer films, molded parts, extruded profiles, coated parts, and foams: windows, luggage racks, wall panels, chair parts, lighting panels, diffusers, shades, partitions, lenses, skylights, lighting devices, reflectors, ductwork, cable trays, conduits, pipes, cable ties, wire coatings, electrical connectors, air handling devices, ventilators, louvers, insulation, bins, storage containers, doors, hinges, handles, sinks, mirror housing, mirrors, toilet seats, hangers, coat hooks, shelving, ladders, hand rails, steps, carts, trays, cookware, food service equipment, communications equipment, and instrument panels.

The compositions are especially useful for articles such as reflectors, e.g., automobile reflectors, an optical lens, a fiber optic connector, and an adhesive.

Where the compositions are used as an adhesive, the article comprises a first substrate having a first surface, a second substrate having a second surface, and a layer of an adhesive composition comprising the polyetherimide disposed between the first surface and the second surface. For example, the adhesive can be used to adhere two polymer substrates, two metal substrates, or a metal substrate and a polymer substrate. There is no particular limitation as to the type of metals or polymers in the substrates. In an embodiment, the adhesive is especially useful in an article having a metal substrate and a fluoropolymer substrate (such as polytetrafluoroethylene (PTFE)) substrate, and an adhesive composition comprising the poly(etherimide) disposed between a surface of the metal substrate and a surface of the fluoropolymer substrate. In a specific embodiment, an article comprises (i) a polytetrafluoroethylene substrate having a first surface, (ii) a metal substrate having a second surface, and (iii) the polymer composition of the invention 1, situated between the polytetrafluoroethylene substrate and the metal substrate. The adhesive layer containing the polymer composition can be in direct contact with the surfaces of the adherends, or an additional layer can be present, for example, a primer.

Without further elaboration, it is believed that one skilled in the art can, using the description herein, utilize the present invention. The following examples are included to provide additional guidance to those skilled in the art of practicing the claims. Accordingly, these examples are not intended to limit the invention in any manner.

Examples

Materials used in the Examples are listed in Table 1. Amounts listed in the Examples are in weight percent (wt. %), based on the total weight of the identified composition.

TABLE 1

| Material | Chemical Description | Source |
|---|---|---|
| ClPAMI Mixture 1 | | SABIC |
| 25 wt. % 3,3'-ClPAMI | 1,3-bis[N-(3-chlorophthalimido)]benzene | |
| 50 wt. % 3,4'-ClPAMI | 1,3-[N-(4-chloro-phthalimido)][N-(3-chlorophthalimido)]benzene | |
| 25 wt. % 4,4'-ClPAMI | 1,3-bis[N-(4-chlorophthalimido)]benzene | |
| ClPAMI Mixture 2 | | SABIC |
| 25 wt. % 3,3'-ClPAMI | 1,3-bis[N-(3-chlorophthalimido)]benzene | |
| 50 wt. % 3,4'-ClPAMI | 1,34N-(4-chloro-phthalimido)][N-(3-chlorophthalimido)]benzene | |
| 25 wt. % 4,4'-ClPAMI | 1,3-bis[N-(4-chlorophthalimido)]benzene | |
| ClPAMI Mixture 3 | | SABIC |
| 25 wt. % 3,3'-ClPAMI | 1,3-bis[N-(3-chlorophthalimido)]benzene | |
| 50 wt. % 3,4'-ClPAMI | 1,34N-(4-chloro-phthalimido)][N-(3-chlorophthalimido)]benzene | |
| 25 wt. % 4,4'-ClPAMI | 1,3-bis[N-(4-chlorophthalimido)]benzene | |
| ClPAMI Mixture 4 | | SABIC |
| 25 wt. % 3,3'-ClPAMI | 1,3-bis[N-(3-chlorophthalimido)]benzene | |
| 50 wt. % 3,4'-ClPAMI | 1,34N-(4-chloro-phthalimido)][N-(3-chlorophthalimido)]benzene | |
| 25 wt. % 4,4'-ClPAMI | 1,3-bis[N-(4-chlorophthalimido)]benzene | |
| ClPAMI Mixture 5 | | SABIC |
| 1 wt. % 3,3'-ClPAMI | 1,3-bis[N-(3-chlorophthalimido)]benzene | |
| 9 wt. % 3,4'-ClPAMI | 1,34N-(4-chloro-phthalimido)][N-(3-chlorophthalimido)]benzene | |
| 90 wt. % 4,4'-ClPAMI | 1,3-bis[N-(4-chlorophthalimido)]benzene | |
| mPD | meta-phenylene diamine | Dupont |
| 4-ClPA | 4-Chlorophthalic anhydride | SABIC |
| 3-ClPA | 3-Chlorophthalic anhydride | SABIC |
| $H_3PO_4$ | Phosphoric Acid | Fischer |
| $Na_2BPA$ | Disodium Bisphenol A | SABIC |
| oDCB | Ortho-dichlorobenzene | Fischer |
| HEGCl | Hexaethylguanidinium Chloride | Atul |

Techniques & Procedures
Gel Permeation Chromatography (GPC) Testing Procedure

The GPC samples were prepared by dissolving 5-10 milligrams (mg) of a sample in 10 milliliters (mL) of dichloromethane. Three to five drops of the polymer solution were added to a 10 mL dichloromethane solution with acetic acid (1-2 drops). The sample solution was then filtered and run, and the analysis was performed by referencing the polymer peak to the oDCB peak. The instrument was a Waters 2695 separations module, which was calibrated with polystyrene standards from Aldrich Chemical Company. The cyclics were analyzed by slicing the GPC traces for cyclics n=2 and 3, but the cyclic n=1 was resolved well enough that it could be integrated separately.

Preparation Procedure for a Mixture of: 3,3'-ClPAMI, 3,4'-ClPAMI and 4,4'-ClPAMI A 250-mL, three-necked flask equipped with a stopper and a gas valve was charged with 3.0 grams (0.0275 moles) of mPD, 5.052 grams (0.0275 moles) 4-CIPA, 5.052 grams (0.0275 moles) of 3-CIPA, 0.011 grams (0.1 mmoles) of SPP, and 60 grams of oDCB. The flask was then equipped with a stir shaft and bearing, nitrogen adapter, and a Dean Stark trap receiver topped with a reflux condenser. A gentle sweep of nitrogen was established through the head-space of the vessel. The reaction was then heated to 100° C. and then ramped to 200° C. over one hour. The oDCB was removed from the mixture until it reached 20-50 wt. % solids (20 grams approximately of oDCB). Note: the random reaction of this mixture of CIPA generates a 1:2:1 ratio of 3,3'-ClPAMI, 3,4'-ClPAMI, and 4,4'-ClPAMI respectively. After 2 to 3 hours, a sample was taken: 30 mg in 20 mL of acetonitrile (sonicated 15 minutes and filtered) and analyzed by HPLC, calibrated for monoamine, (monoamine is the mono-imide of halo-phthalic anhydride with a di-amine, such as mPD) 3, CIPA, 4-CIPA, and mPD. Once the amounts of analytes were known, the appropriate correction was made with either mPD or 4-CIPA. This was repeated until the 3-monoamine, 4-monoamine, 3-CIPA, and 4-CIPA were within the specification limit of the reaction, 0.2 mole percent. The reaction was then cooled and kept under a static nitrogen atmosphere.

Isomer mixtures other than the 1:2:1 random distribution illustrated above can be produced according to techniques known in the art, for example, by using a similar procedure to prepare the 3,3' and 4,4'-ClPAMI isomers separately, and/or by employing different proportions of 3- and 4-CIPA starting materials to produce a product containing a different proportion of the three isomers, then blending the products of differing isomer compositions to produce another desired proportion of isomers in a polymer mixture.

Polymerization Procedure

Polyetherimides were made as follows. Once the mixture of 3,3', 3,4', and 4,4'-isomers was made, the reaction vessel was then transferred to the dry box where the salt of 7.35 grams (0.0270 moles) of Na$_2$BPA was added. The reaction was then heated to 200° C. with a nitrogen gentle sweep, to remove some oDCB, drying the mixture. oDCB was removed from the mixture until it reached 30-50 weight percent of solids. Once the overheads were dry by Karl Fischer analysis (less than 50 ppm), 71 mg (1 mole %) of HEGC1 was charged to the solution; within 30 minutes the solution was brownish and finally a golden solution after 90 minutes. The mixture was sampled after 2 hours to measure Mw, then Mw analysis was repeated every hour until the reaction plateaued (plateau=3 samples within 300 amu), if the Mw was below 45,000 amu, a correction of Na$_2$BPA was made. The reaction was then quenched with 134 mg (1 mole % respect to polymer) of H$_3$PO$_4$ (85% aqueous) concentrated. Once the acid was added, a nitrogen purge was added to remove any water (5 minutes). The reaction was heated for another hour. The reaction was then cooled and diluted to 10 wt. % with oDCB (approximately 70 mL). The mixture was then filtered on a Buchner funnel using a Whatman 1 micrometer GF (glass filter) disk. The golden solution was then transferred to a 1-liter separatory funnel with equal volume of acidic water, and vigorously shaken. Once the contents of the separatory funnel split into phases, the golden polymer solution was transferred to a blender with an equal volume of hexane and blended. The mixture was filtered and dried under vacuum at 165° C. for 24 hours.

Testing Procedures
Samples that were Prepared were Tested as Follows.
Rheology Testing Procedure The viscosity was measured using parallel plate rheometry at 340° C., and viscosity ratio was calculated from readings taken at 1 rad/s to 316 radian/sec. This viscosity ratio gives a measure of shear thinning or improved flow properties with 3 isomer rich polymer as compared to 4 isomer rich product.

T$_g$ Testing Procedure

Glass transition temperature (T$_g$) was measured on a 10 mg sample at a heating rate of 20° C./min.

The polymers prepared were targeted for 55,000 Mw, (polystyrene standards were used for calibration), but some were slightly higher and lower Mw. The PDI of the 3-CIPA enriched polymers were higher than the 1000 grade control because of the cyclic n=1. The cyclic n=1 is an adduct of one BPA and 3,3'-ClPAMI; and is characteristic of only the 3-CIPA enriched polymer systems due to the high concentration of 3,3'-ClPAMI.

Examples 1-5

The purpose of Examples 1-5 was to make polyetherimides with enriched 3-CIPA component in an amount that is more than 45% and less than 75% with 0 to 3 mole % of NaPCP and 0 to 2 mole % excess Na$_2$BPA salt and evaluate how these factors affect the total chloride and hydroxyl end-group content of the polyetherimide.

Five polyetherimides were made using the procedures described above from bis(chlorophthalimide) compositions as shown in Table 2. Properties of the polyetherimides are also shown in Table 2.

TABLE 2

| Example | 1 (Invention) | 2 (Comparative) | 3 (Comparative) | 4 (Comparative) | 5 (Comparative) |
|---|---|---|---|---|---|
| 3,3'-ClPAMI | 25 | 25 | 25 | 25 | 1 |
| 3,4'-ClPAMI | 50 | 50 | 50 | 50 | 9 |
| 4,4'-ClPAMI | 25 | 25 | 25 | 25 | 90 |
| Na$_2$BPA excess | Yes | Yes | No | No | No |
| NaPCP excess | Yes | No | Yes | No | No |
| Mw | 43053 | 42651 | 46369 | 44299 | 45000 |
| Mn | 10996 | 10852 | 11449 | 10614 | 18000 |

TABLE 2-continued

| Example | 1 (Invention) | 2 (Comparative) | 3 (Comparative) | 4 (Comparative) | 5 (Comparative) |
|---|---|---|---|---|---|
| Polydispersity Index (PDI) | 3.91 | 3.93 | 4.05 | 4.17 | 2.5 |
| Total Cl (ppm) | 750 | 1620 | 1700 | 3660 | 3480 |
| Total OH end-groups (ppm) | 650 | 1775 | 364 | 387 | 350 |
| Tg (° C.) | 225 | 225 | 225 | 226 | 217 |
| Rheology Ratio | 3 | 3 | 3 | 3 | 2 |

Discussion

The molecular weights of the polyetherimides were similar, as evidenced by the GPC data.

The results of Example 1 show that when the PEI was made with a mixture containing at least 50 wt. % of 3,4'-CIPAMI, at least 25 wt. % of 3,3'-CIPAMI, and with a maximum of 25 wt. % of 4,4'-CIPAMI, in the presence of a two mole % excess of Na$_2$BPA salt and three mole % of NaPCP with respect to CIPAMI, the resulting PEI had a total chloride content of 750 ppm and a hydroxyl endgroup level of 650 ppm. The Tg of Example 1 was 225° C., which represents an 8 degree increase over that in Comparative Example 5. Further, this PEI exhibited greater shear thinning than did Comparative Example 5, that is; whereas a PEI made from a CIPAMI component having 3,4'-CIPAMI in an amount less than 10 wt. % (Comparative Example 5) has a rheology ratio of 2, which is at least 30% lower than the rheology ratio of 3 in Example 1.

The results for Comparative Example 2 show that when the PEI was made with a mixture containing at least 50 wt. % of 3,4'-CIPAMI, at least 25 wt. % of 3,3'-CIPAMI, a maximum of 25 wt. % of 4,4'-CIPAMI, and a two mole % excess of Na$_2$BPA with respect to CIPAMI, the resulting PEI had a total chloride content of 1620 ppm and a hydroxyl endgroup level of 1775 ppm.

The results for Comparative Example 3 show that when the PEI was made with a mixture containing at least 50 wt. % of 3,4'-CIPAMI, at least 25 wt. % of 3,3'-CIPAMI, a maximum of 25 wt. % of 4,4'-CIPAMI, and a three mole % excess of NaPCP with respect to CIPAMI, the resulting PEI had a total chloride content of 1700 ppm and a hydroxyl endgroup level of 364 ppm.

The results for Comparative Example 4 show that when the PEI was made with a mixture containing at least 50 wt. % of 3,4'-CIPAMI, at least 25 wt. % of 3,3'-CIPAMI and a maximum of 25 wt. % of 4,4'-CIPAMI, the resulting PEI had a total chloride content of 3660 ppm and a hydroxyl endgroup level of 387 ppm.

The results for Comparative Example 5 show that when the PEI was made with a mixture containing at least 90 wt. % of 4,4'-CIPAMI, at least 1 wt. % of 3,3'-CIPAMI, and less than 10 wt. % of 3,4'-CIPAMI, the resulting PEI had a total chloride content of 3480 ppm and a hydroxyl endgroup level of 350 ppm. The Tg of Comparative Example 5 was 217° C., 8 degrees lower than Examples 1-4. Further, the PEI exhibited a higher shear rate viscosity; whereas PEIs made from a CIPAMI component having at least 50% of 3,4'-CIPAMI (Examples 1-4) have a lower shear rate viscosity at least 30% lower than Comparative Example 5.

As illustrated above, Example 1, which represents an embodiment of the invention, demonstrated the utility of using the combined factors of two mole % excess of Na$_2$BPA salt and three mole % of NaPCP for the polymerization reaction to achieve a low chloride level of 750 ppm while maintaining a low hydroxyl endgroup level of 650 ppm. While Comparative Examples 2 and 3 demonstrated that when either of the two factors (two mole % excess of Na$_2$BPA salt and three mole % of NaPCP) were used separately, a higher chloride level of 1620 to 1700 ppm was attained. To further demonstrate the effect, Comparative Examples 4 and 5 used neither of the factors resulting in a dramatically higher chloride level of 3480 to 3660 ppm. Example 1 also demonstrated that the higher Tg of 225° C. and greater shear thinning, as indicated by the higher rheology ratio of 3, achieved by polymers of Comparative Examples 2-4 are maintained, while achieving the improved low chloride and hydroxyl endgroup composition of Example 1. FIG. 1 summarizes the substantially less chlorine and OH substituents that compositions of our invention exhibited as compared to compositions of Comparative Examples 2-5.

All patents and references cited herein are incorporated by reference.

Embodiment 1

A polymer composition comprising a polyetherimide having the formula

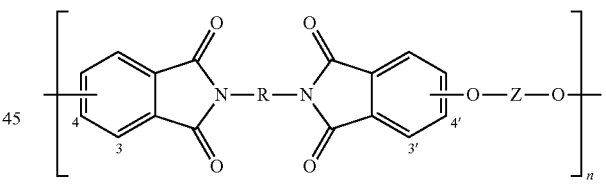

wherein n is greater than 1, each R is the same or different, and is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

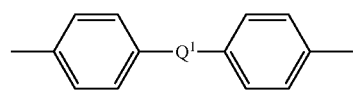

wherein $Q^1$ is selected from —O—, —S—, —C(O)—, —SO$_2$—, —SO—, and —C$_y$H$_{2y}$— wherein y is 1 to 5 and a halogenated derivative thereof, each Z is the same or different, and is an aromatic C$_{6-24}$ monocyclic or polycyclic moiety optionally substituted with 1 to 6 C$_{1-18}$ alkyl groups, 1 to 8 halogen atoms, or a combination thereof, and the divalent bonds between the —O—Z—O— group and the phenyl substituents are in the 3,3', 3,4', 4,3', and 4,4' positions, the divalent bonds of the —O—Z—O— group being made from a bis(halophthalimide) composition comprising, based on the weight of the bis(halophthalimide) composition, at least 15 wt. % of a 3,3'-bis(halophthalimide) of the formula

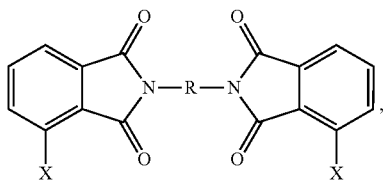

from more than 17 wt. % to less than 85 wt. % of a 4,3'-bis(halophthalimide) of the formula

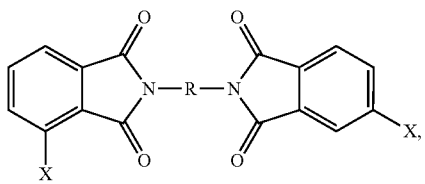

and
from more than 0 to less than 27 wt. % of a 4,4'-bis(halophthalimide) of the formula

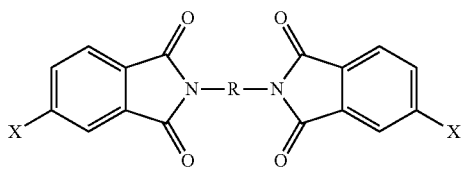

wherein each X is independently fluoro, chloro, bromo, or iodo and R is as defined above, the polyetherimide being a catalyzed polymerization reaction product of the bis(halophthalimide) composition and a 1.6 to 2.0 mole % excess of an alkali metal salt of a dihydroxy aromatic compound of the formula

MO—Z—OM wherein M is an alkali metal, and Z is as defined above, in the presence of from 2 to 4 mole % of an endcapping agent, and wherein the polyetherimide has: a Tg above 220° C.; 20 wt. % to 35 wt. % solids; an Mw of at least 42,000 Daltons; a maximum chloride content of less than 900 ppm by weight; a maximum of 700 ppm by weight OH endgroup polymer functionality; and the low shear viscosity of the polyetherimide is at least 30% lower than a polyetherimide made from a bis(halophthalimide) composition comprising less than 10 wt. % of the 4,3'-bis(halophthalimide).

Embodiment 2

The composition of embodiment 1, wherein the bis(halophthalimide) composition comprises from more than 47 wt. % to less than 85 wt. % of the 4,3'-bis(halophthalimide).

Embodiment 3

The composition of embodiment 1, wherein the bis(halophthalimide) composition comprises from 15 to less than 85 wt. % of the 3,3'-bis(halophthalimide), from more than 47 to less than 85 wt. % of the 4,3'-bis(halophthalimide), and from more than 0 to less than 27 wt. % of the 4,4'-bis(halophthalimide).

Embodiment 4

The composition of embodiment 1, wherein R is a divalent radical of the formula

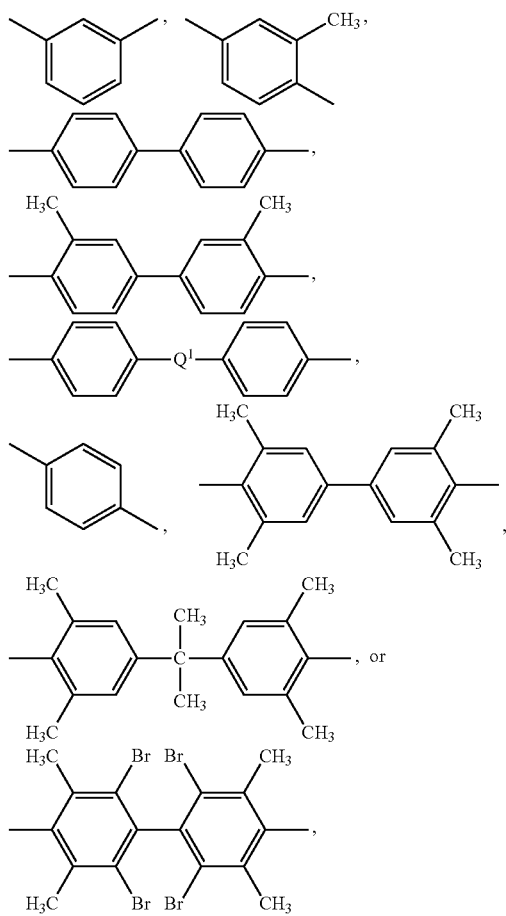

wherein $Q^1$ is selected from —O—, —S—, —C(O)—, —SO$_2$—, —SO—, and —C$_y$H$_{2y}$— wherein y is an integer from 1 to 5 and a halogenated derivative thereof; and Z is a divalent group of formula

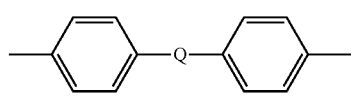

wherein Q is —O—, —S—, —C(O)—, —SO$_2$—, —SO—, or —C$_y$H$_{2y}$— wherein y is an integer from 1 to 5 and a halogenated derivative thereof.

Embodiment 5

The composition of embodiment 1, wherein Z is 2,2-(4-phenylene)isopropylidene and R is m-phenylene, p-phenylene diarylsulfone, or a combination thereof.

Embodiment 6

The composition of embodiment 1, further comprising an additive selected from impact modifiers, fillers, reinforcing agents, anti-oxidants, heat stabilizers, light stabilizers, ultraviolet light absorbers, plasticizers, lubricants, mold release agents, antistatic agents, colorants, blowing agents, flame retardants, anti-drip agents, and radiation stabilizers, and a combination thereof.

Embodiment 7

The composition of embodiment 1, further comprising an additive selected from an antioxidant, an ultraviolet light absorber, a mold release agent, and a combination thereof.

Embodiment 8

The composition of embodiment 1, wherein the bis(halophthalimide) composition comprises, based on the weight of the bis(halophthalimide) composition, at least 15 wt. % of a 3,3'-bis(chlorophthalimide) of the formula

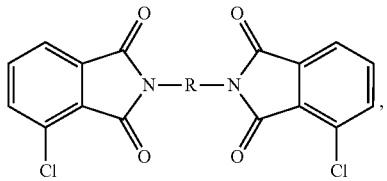

from more than 17 wt. % to less than 85 wt. % of a 4,3'-bis(chlorophthalimide) of the formula

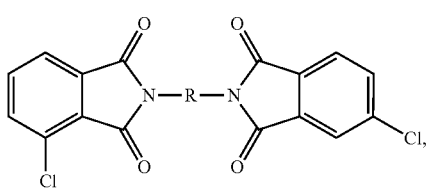

and
from more than 0 to less than 27 wt. % of a (4,4'-bis(chlorophthalimide) of the formula

wherein R is as defined above.

Embodiment 9

The composition of embodiment 8, wherein the bis(chlorophthalimide) composition comprises, from 15 to less than 85 wt. % of the 3,3'-bis(chlorophthalimide), from 47 to less than 85 wt. % of the 4,3-bis(chlorophthalimide), and from more than 0 to less than 27 wt. % of the 4,4'-bis(chlorophthalimide).

Embodiment 10

A method for the manufacture of a polyetherimide composition, the method comprising reacting: from 1.6 to 2.0 mole % excess of an alkali metal salt of a dihydroxy aromatic compound of the formula

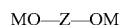

wherein M is an alkali metal and Z is an aromatic $C_{6-24}$ monocyclic or polycyclic moiety optionally substituted with 1 to 6 $C_{1-8}$ alkyl groups, 1 to 8 halogen atoms, or a combination thereof; with a bis(halophthalimide) composition comprising, based on the weight of the bis(halophthalimide) composition, at least 15 wt. % of a 3,3'-bis(halophthalimide) of the formula

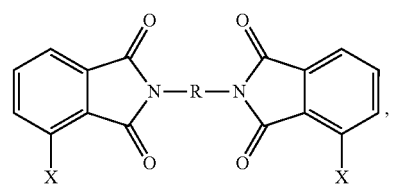

from more than 17 wt. % to less than 85 wt. % of a 4,3'-bis(halophthalimide) of the formula

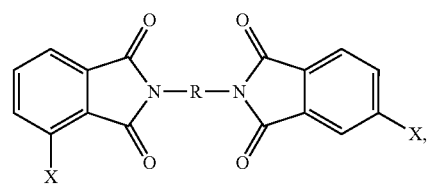

and
from more than 0 to less than 27 wt. % of a 4,4'-bis(halophthalimide) of the formula

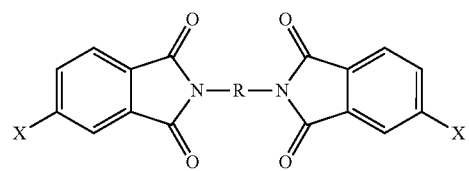

wherein each R is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

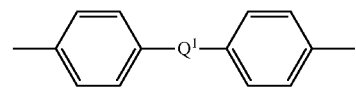

wherein $Q^1$ is selected from —O—, —S—, —C(O)—, —SO$_2$—, —SO—, and —C$_y$H$_{2y}$— wherein y is 1 to 5 and a halogenated derivative thereof, and each X is independently fluoro, chloro, bromo, or iodo; and adding from 2 to 4 mole % of a derivative of sodium phenoxide to the polyetherimide; to produce a polyetherimide of the formula

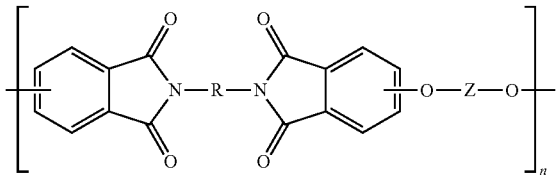

wherein n is greater than 1, each R is the same or different and is as defined above, each Z is the same or different, and is as defined above, and the divalent bonds between the —O—Z—O— group and the phenyl substituents are in the 3,3', 3,4', 4,3', and 4,4' positions; wherein the polyetherimide has: a Tg of greater than 220° C.; 20 to 35 wt. % solids; an Mw of at least 42,000 Daltons; a maximum chloride content of 900 ppm; a maximum of 700 ppm OH endgroup polymer functionality; and the low shear viscosity of the polyetherimide is at least 30% lower than a polyetherimide made from a bis (halophthalimide) composition comprising less than 10% of 4,3'-bis(halophthalimide.

Embodiment 11

The method of embodiment 10, wherein the derivative of sodium phenoxide is sodium para cumyl phenol.

Embodiment 12

An article comprising the composition of embodiment 1.

Embodiment 13

The article of embodiment 12, selected from a sheet, film, multilayer sheet, multilayer film, molded part, extruded profile, coated part, and fiber.

Embodiment 14

The article of embodiment 13, wherein the article is a molded part having a thickness from 1 to 5 millimeters.

Embodiment 15

The article of embodiment 14, selected from a reflector, an optical lens, a fiber optic connector, and an adhesive.

Embodiment 16

The article of embodiment 14, wherein the article is a connector for electronic or electrical applications.

Embodiment 17

The article of embodiment 15, the article comprising (i) a polytetrafluoroethylene substrate having a first surface, (ii) a metal substrate having a second surface, and (iii) the polymer composition of the invention, situated between the polytetrafluoroethylene substrate and the metal substrate.

Embodiment 18

A method of forming an article, comprising shaping, extruding, blow molding, or molding the composition of embodiment 1 to form the article.

Embodiment 19

The method of embodiment 18, further comprising molding the composition to form an article having a thickness from 1 to 5 millimeters.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A polymer composition comprising a polyetherimide having the formula

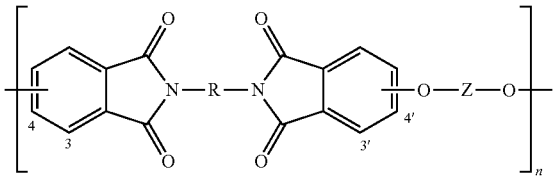

wherein n is greater than 1, each R is the same or different, and is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

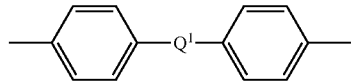

wherein $Q^1$ is selected from —O—, —S—, —C(O)—, —SO$_2$—, —SO—, and —C$_y$H$_{2y}$— wherein y is 1 to 5 and a halogenated derivative thereof, each Z is the same or different, and is an aromatic C$_{6-24}$ monocyclic or polycyclic moiety optionally substituted with 1 to 6 C$_{1-18}$ alkyl groups, 1 to 8 halogen atoms, or a combination thereof, and the divalent bonds between the —O—Z—O— group and the phenyl substituents are in the 3,3', 3,4', 4,3', and 4,4' positions, the divalent bonds of the —O—Z—O— group being made from a bis(halophthalimide) composition comprising, based on the weight of the bis(halophthalimide) composition, at least 15 wt. % of a 3,3'-bis(halophthalimide) of the formula

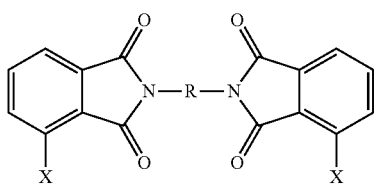

from more than 17 wt. % to less than 85 wt. % of a 4,3'-bis(halophthalimide) of the formula

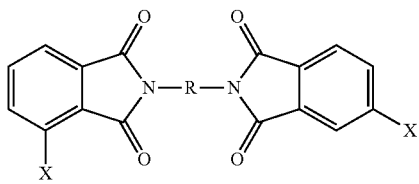

and from more than 0 to less than 27 wt. % of a 4,4'-bis (halophthalimide) of the formula

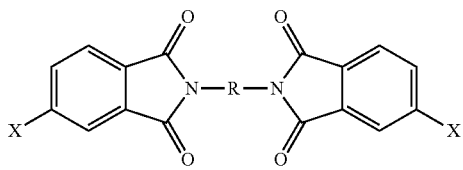

wherein each X is independently fluoro, chloro, bromo, or iodo and R is as defined above, the polyetherimide being a catalyzed polymerization reaction product of the bis(halophthalimide) composition and a 1.6 to 2.0 mole % excess of an alkali metal salt of a dihydroxy aromatic compound of the formula

MO—Z—OM wherein M is an alkali metal, and Z is as defined above,
in the presence of from 2 to 4 mole % of an endcapping agent selected from derivatives of sodium phenoxide, and
wherein the polyetherimide has:
a Tg above 220° C.;
20 wt. % to 35 wt. % solids;
an Mw of at least 42,000 Daltons;
a maximum chloride content of less than 900 ppm by weight;
a maximum of 700 ppm by weight OH endgroup polymer functionality; and
the low shear viscosity of the polyetherimide is at least 30% lower than a polyetherimide made from a bis(halophthalimide) composition comprising less than 10 wt. % of the 4,3'-bis(halophthalimide).

2. The composition of claim 1, wherein the bis(halophthalimide) composition comprises from more than 47 wt. % to less than 85 wt. % of the 4,3'-bis(halophthalimide).

3. The composition of claim 1, wherein the bis(halophthalimide) composition comprises
from 15 to less than 85 wt. % of the 3,3'-bis(halophthalimide),
from more than 47 to less than 85 wt. % of the 4,3'-bis (halophthalimide), and
from more than 0 to less than 27 wt. % of the 4,4'-bis (halophthalimide).

4. The composition of claim 1, wherein R is a divalent radical of the formula

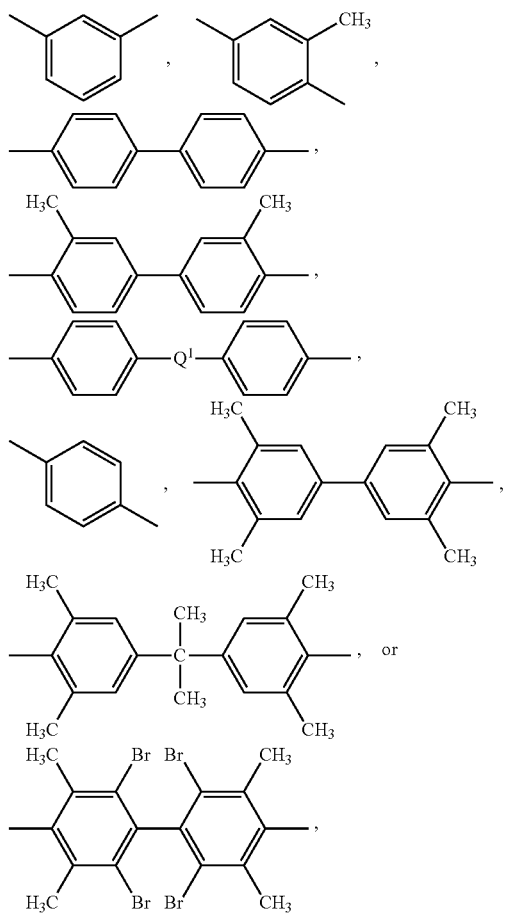

wherein Q' is selected from —O—, —S—, —C(O)—, —SO$_2$—, —SO—, and —C$_y$H$_{2y}$— wherein y is an integer from 1 to 5 and a halogenated derivative thereof; and
Z is a divalent group of formula

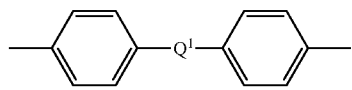

wherein Q is —O—, —S—, —C(O)—, —SO$_2$—, —SO—, or —C$_y$H$_{2y}$— wherein y is an integer from 1 to 5 and a halogenated derivative thereof.

5. The composition of claim 1, wherein Z is 2,2-(4-phenylene)isopropylidene and R is m-phenylene, p-phenylene diarylsulfone, or a combination thereof.

6. The composition of claim 1, further comprising an additive selected from impact modifiers, fillers, reinforcing agents, anti-oxidants, heat stabilizers, light stabilizers, ultraviolet light absorbers, plasticizers, lubricants, mold release agents, antistatic agents, colorants, blowing agents, flame retardants, anti-drip agents, and radiation stabilizers, and a combination thereof.

7. The composition of claim 1, further comprising an additive selected from an antioxidant, an ultraviolet light absorber, a mold release agent, and a combination thereof.

8. The composition of claim 1, wherein the bis(halophthalimide) composition comprises, based on the weight of the bis(halophthalimide) composition, at least 15 wt. % of a 3,3'-bis(chlorophthalimide) of the formula

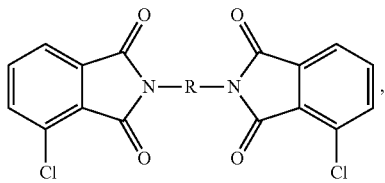, from more than 17 wt. % to less than 85 wt. % of a 4,3'-bis(chlorophthalimide) of the formula

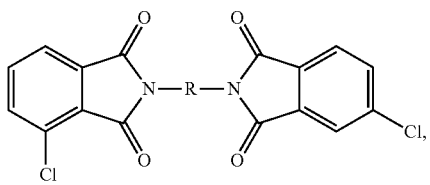, and from more than 0 to less than 27 wt. % of a (4,4'-bis(chlorophthalimide) of the formula

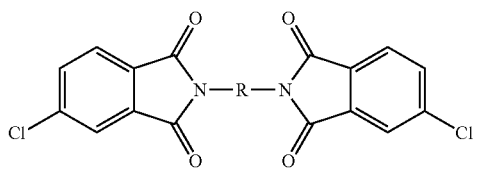

wherein R is as defined above.

9. The composition of claim 8, wherein the bis(chlorophthalimide) composition comprises from 15 to less than 85 wt. % of the 3,3'-bis(chlorophthalimide), from 47 to less than 85 wt. % of the 4,3-bis(chlorophthalimide), and from more than 0 to less than 27 wt. % of the 4,4'-bis(chlorophthalimide).

10. A method for the manufacture of a polyetherimide composition, the method comprising reacting:

from 1.6 to 2.0 mole % excess of an alkali metal salt of a dihydroxy aromatic compound of the formula

MO—Z—OM wherein M is an alkali metal and Z is an aromatic $C_{6-24}$ monocyclic or polycyclic moiety optionally substituted with 1 to 6 $C_{1-8}$ alkyl groups, 1 to 8 halogen atoms, or a combination thereof;

with a bis(halophthalimide) composition comprising, based on the weight of the bis(halophthalimide) composition, at least 15 wt. % of a 3,3'-bis(halophthalimide) of the formula

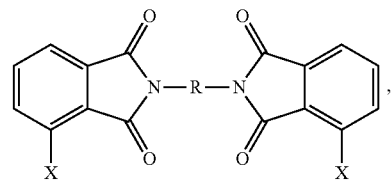, from more than 17 wt. % to less than 85 wt. % of a 4,3'-bis(halophthalimide) of the formula

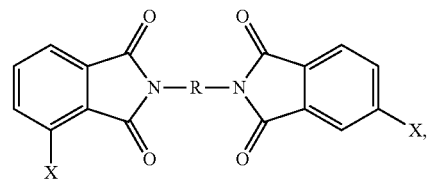

and from more than 0 to less than 27 wt. % of a 4,4'-bis(halophthalimide) of the formula

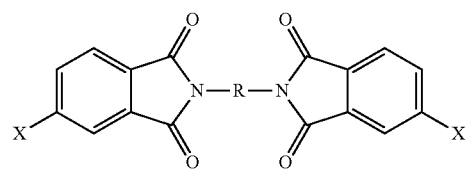

wherein each R is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

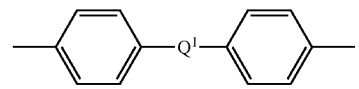

wherein $Q^1$ is selected from —O—, —S—, —C(O)—, —SO$_2$—, —SO—, and —C$_y$H$_{2y}$— wherein y is 1 to 5 and a halogenated derivative thereof, and each X is independently fluoro, chloro, bromo, or iodo; and adding from 2 to 4 mole % of a derivative of sodium phenoxide to the polyetherimide; to produce a polyetherimide of the formula

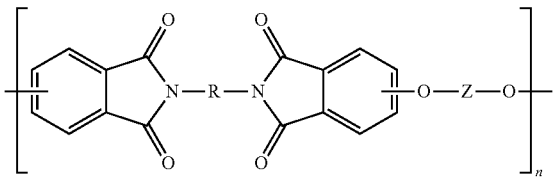

wherein n is greater than 1, each R is the same or different and is as defined above, each Z is the same or different, and is as defined above, and the divalent bonds between the —O—Z—O— group and the phenyl substituents are in the 3,3', 3,4', 4,3', and 4,4' positions;

wherein the polyetherimide has:
- a Tg of greater than 220° C.;
- 20 to 35 wt. % solids;
- an Mw of at least 42,000 Daltons;
- a maximum chloride content of 900 ppm;
- a maximum of 700 ppm OH endgroup polymer functionality; and the low shear viscosity of the polyetherimide is at least 30% lower than a polyetherimide made from a bis(halophthalimide) composition comprising less than 10% of 4,3'-bis(halophthalimide.

11. The method of claim 10, wherein the derivative of sodium phenoxide is sodium para cumyl phenol.

12. An article comprising the composition of claim 1.

13. The article of claim 12, selected from a sheet, film, multilayer sheet, multilayer film, molded part, extruded profile, coated part, and fiber.

14. The article of claim 13, wherein the article is a molded part having a thickness from 1 to 5 millimeters.

15. The article of claim 14, selected from a reflector, an optical lens, a fiber optic connector, and an adhesive.

16. The article of claim 14, wherein the article is a connector for electronic or electrical applications.

17. The article of claim 15, the article comprising
   (i) a polytetrafluoroethylene substrate having a first surface,
   (ii) a metal substrate having a second surface, and
   (iii) the polymer composition situated between the polytetrafluoroethylene substrate and the metal substrate.

18. A method of forming an article, comprising shaping, extruding, blow molding, or molding the composition of claim 1 to form the article.

19. The method of claim 18, further comprising molding the composition to form an article having a thickness from 1 to 5 millimeters.

* * * * *